Figure 1A:
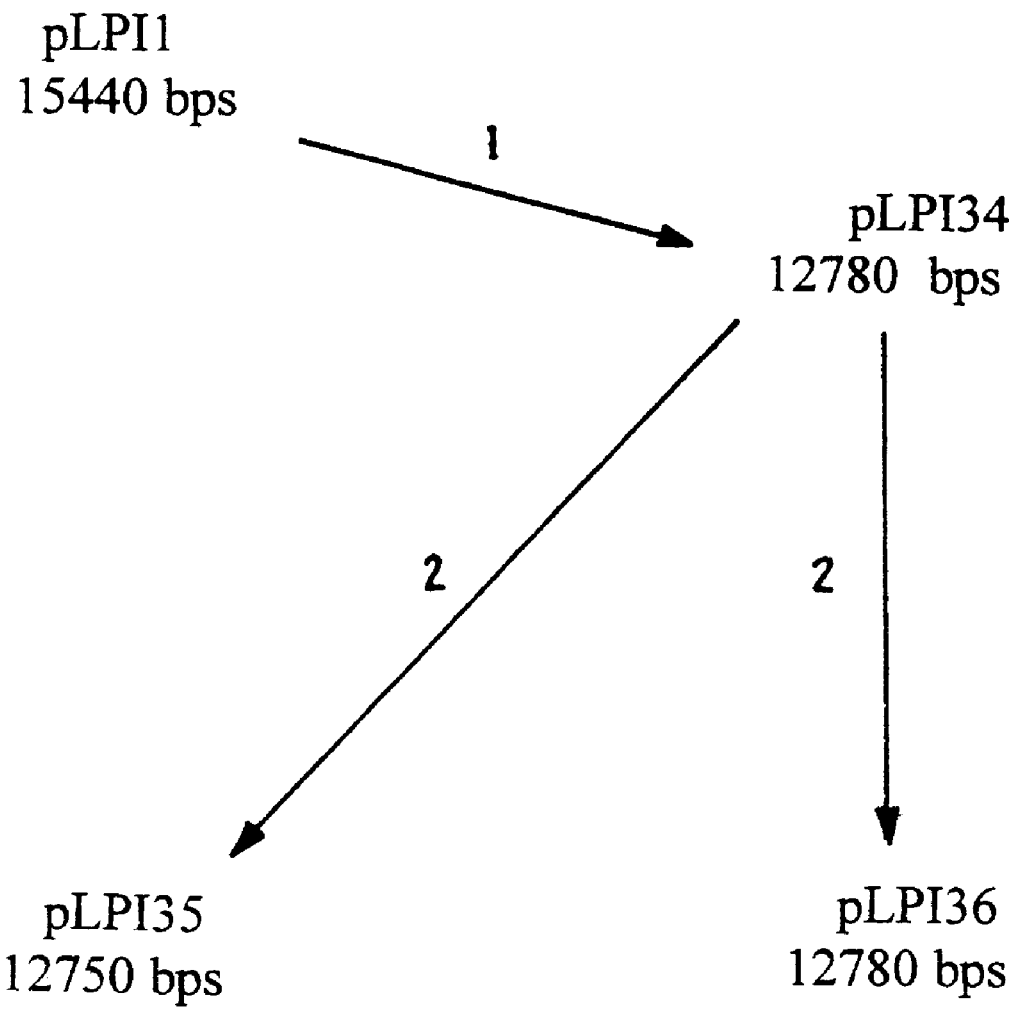
Figure 1B:
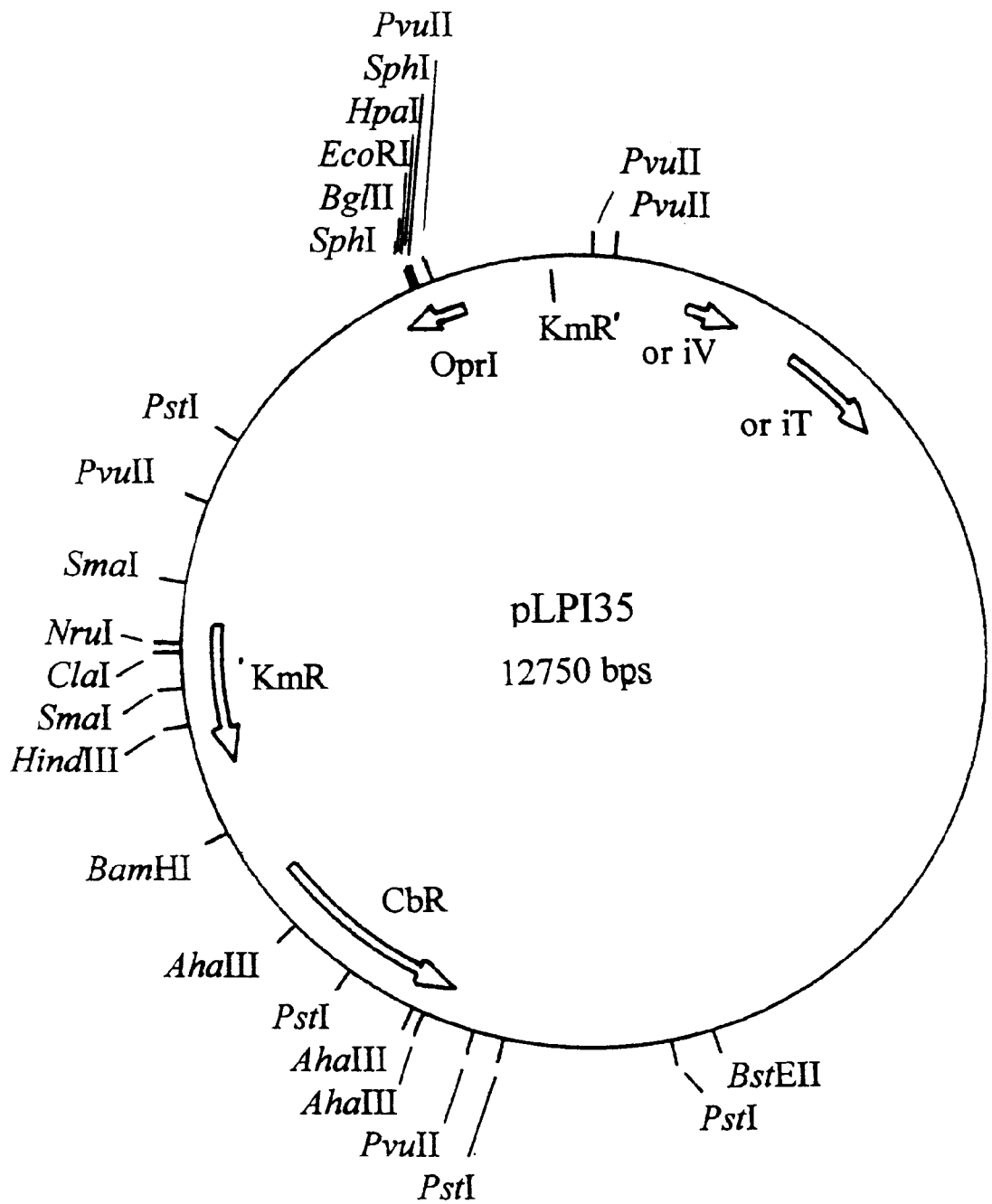
Figure 1C:
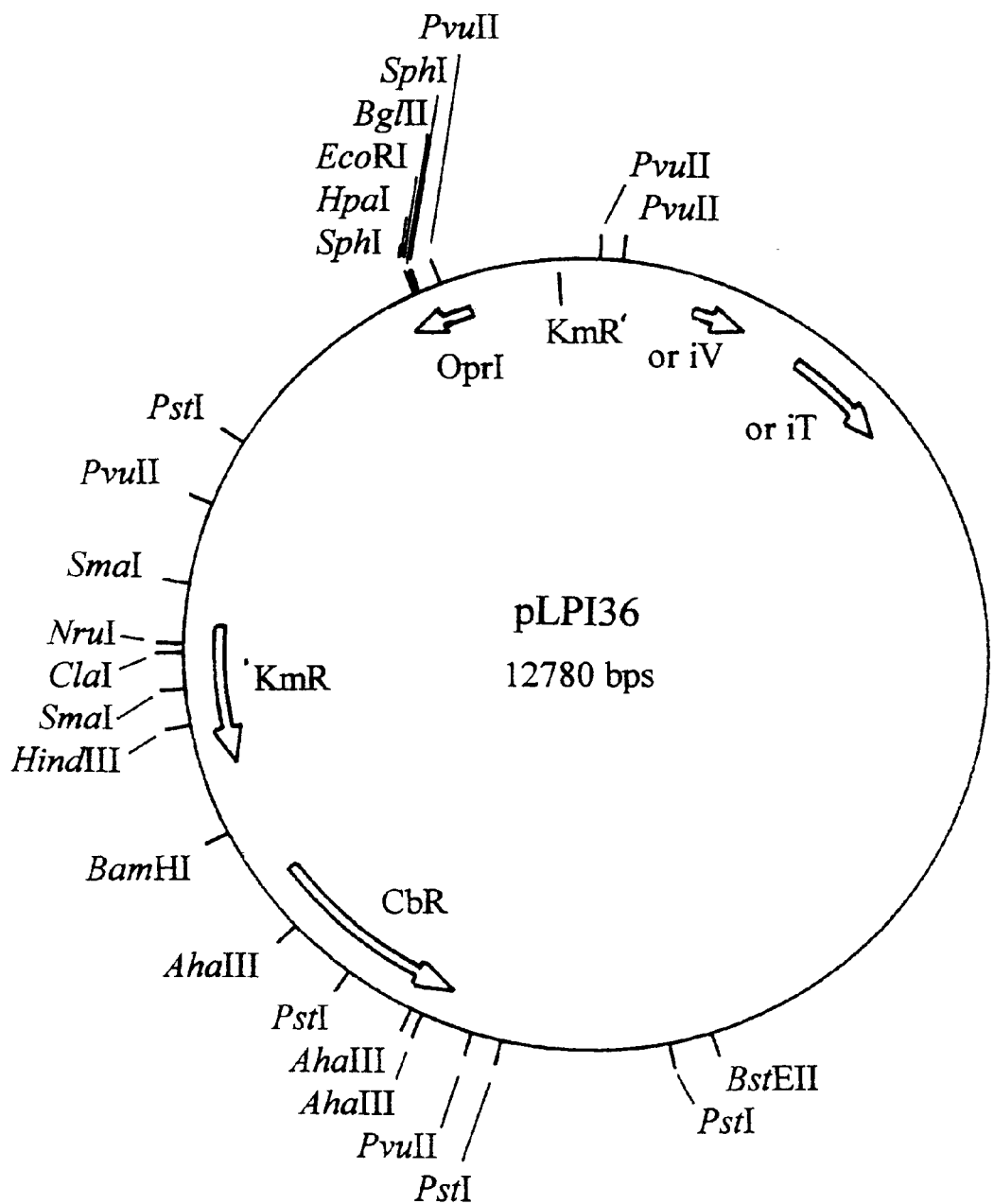
Figure 1D:
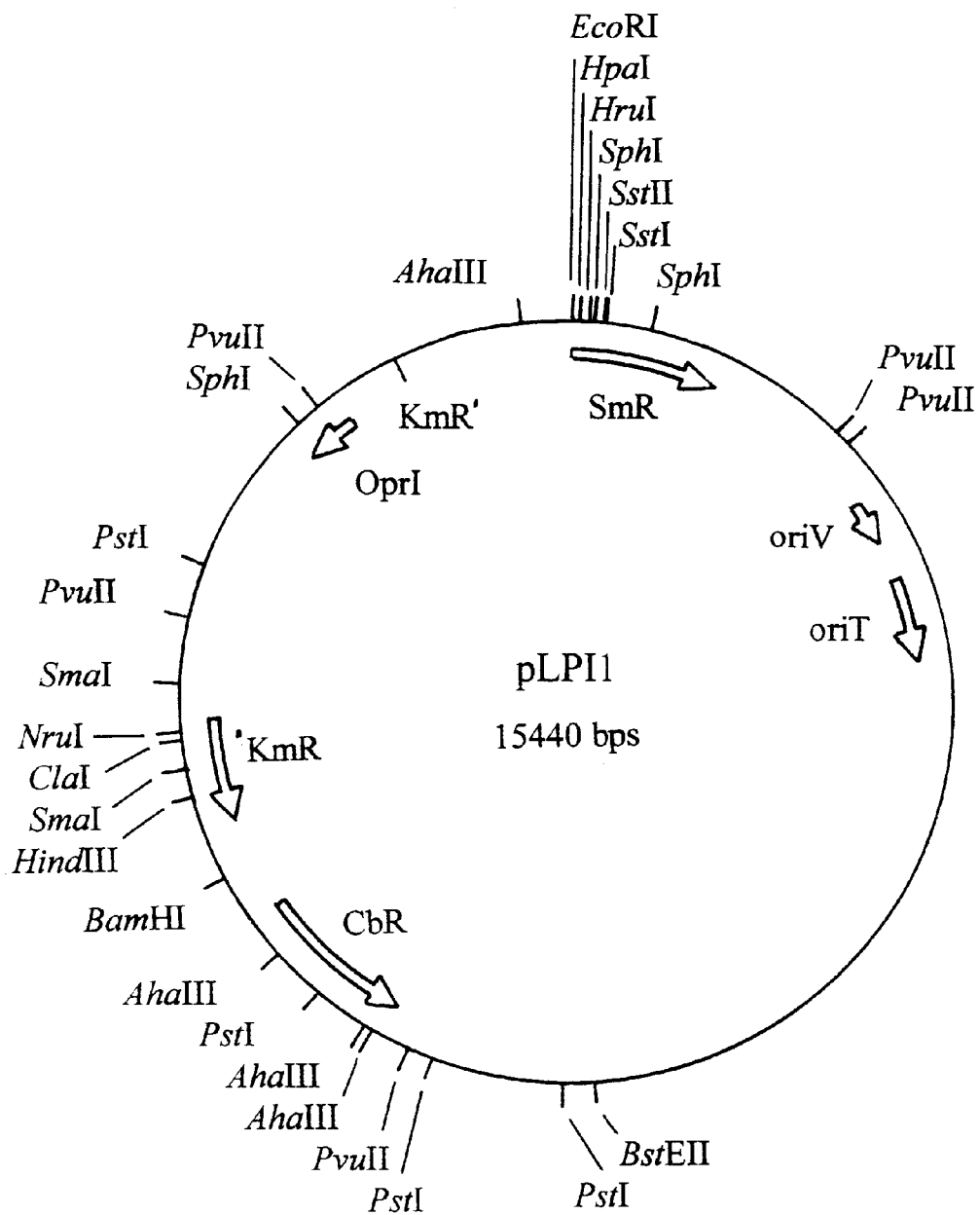
Figure 1E:
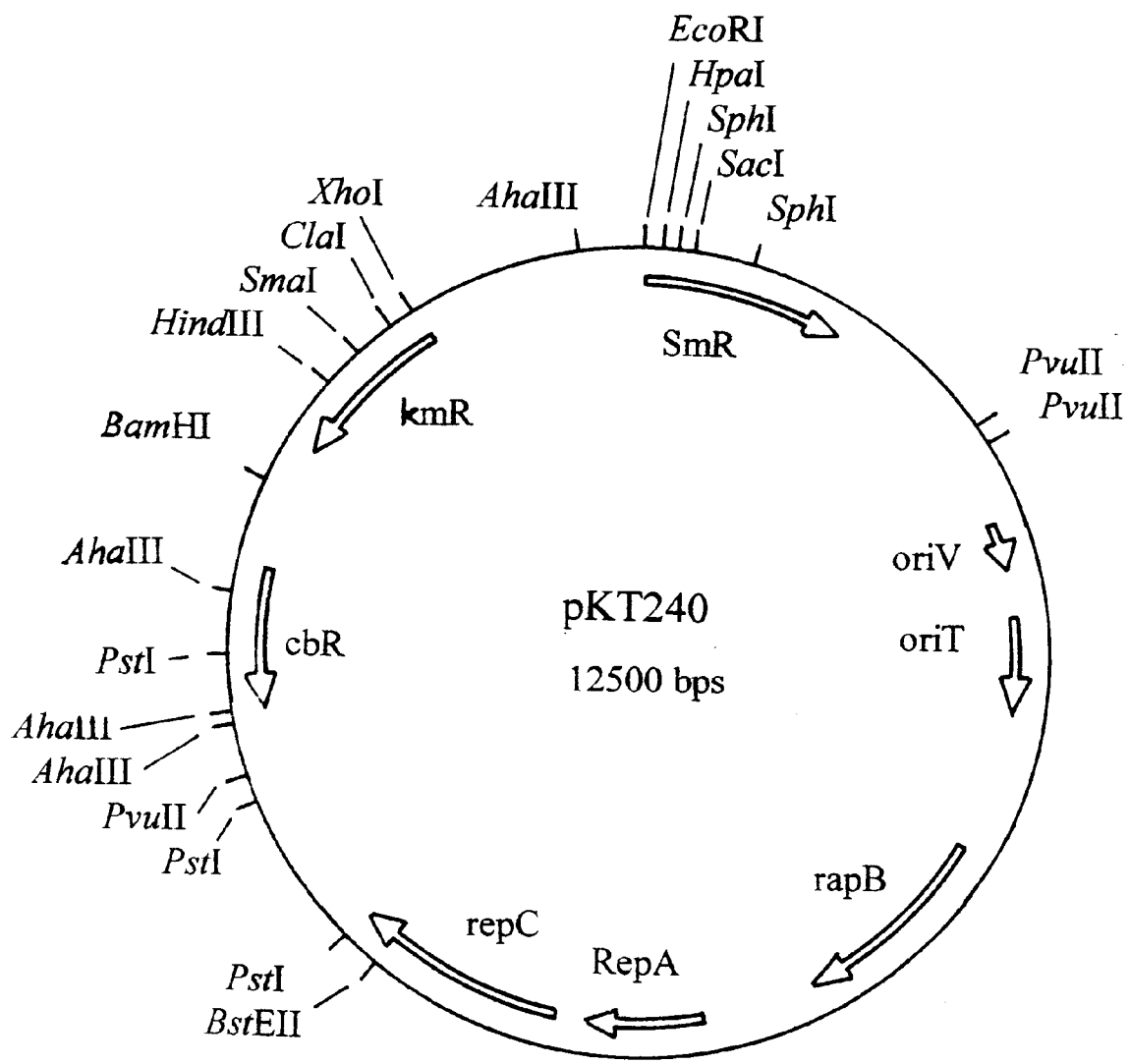
Figure 1F:
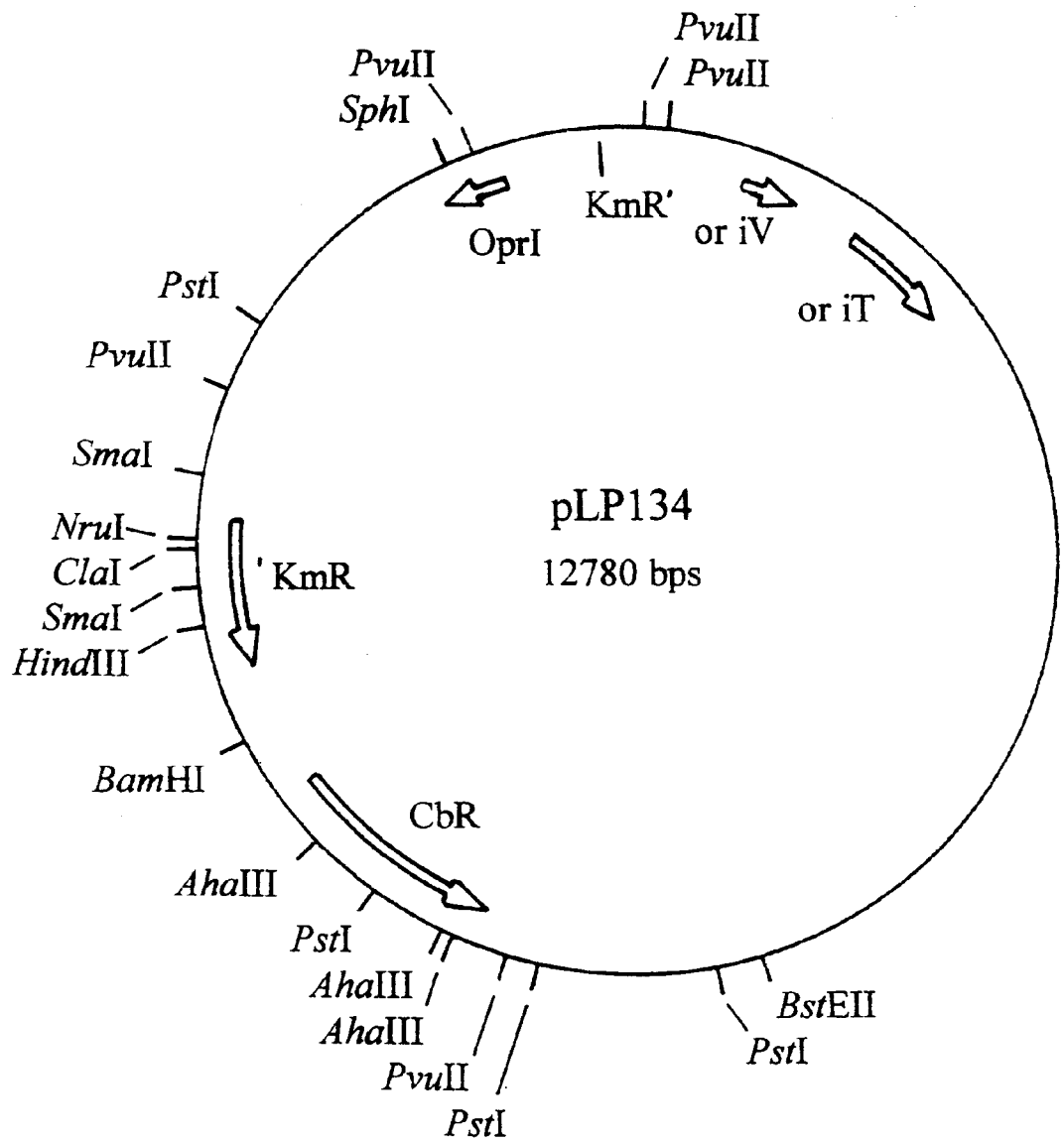

United States Patent [19]

Hamers et al.

[11] Patent Number: 6,130,085

[45] Date of Patent: Oct. 10, 2000

[54] RECOMBINANT VECTOR CONTAINING A SEQUENCE OF A LIPOPROTEIN GENE FOR THE EXPRESSION OF NUCLEOTIDE SEQUENCES

[76] Inventors: Raymond Hamers, Vijversweg 15; Pierre Cornelis, Paardenstraat 65, both of B-1640 Sint-Genesius-Rode, Belgium

[21] Appl. No.: 08/592,400

[22] PCT Filed: Aug. 2, 1994

[86] PCT No.: PCT/EP94/02550

§ 371 Date: Apr. 8, 1996

§ 102(e) Date: Apr. 8, 1996

[87] PCT Pub. No.: WO95/04079

PCT Pub. Date: Feb. 9, 1995

[30] Foreign Application Priority Data

Aug. 2, 1993 [FR] France ................................. 93 09511

[51] Int. Cl.[7] .................................................. C12N 15/00
[52] U.S. Cl. ................... 435/320.1; 435/69.1; 435/69.7; 435/71.1; 435/252.3; 435/252.33; 435/252.34; 435/252.8; 435/253.3; 435/875; 435/849; 435/471; 435/481; 435/488; 530/350
[58] Field of Search ............................. 435/320.1, 172.1, 435/172.3, 252.3, 252.8, 253.3, 69.1, 69.7, 71.1, 875, 849, 471, 481, 488, 252.33, 252.34; 530/350

[56] References Cited

U.S. PATENT DOCUMENTS 5,348,867 9/1994 Georgiou ............................... 435/69.7
5,583,038 12/1996 Stover ................................... 435/252.3

FOREIGN PATENT DOCUMENTS

400973A1 12/1990 European Pat. Off. .
4122598 7/1992 Germany .
WO8403519 9/1984 WIPO .
WO9109952 7/1991 WIPO .
WO9307897 4/1993 WIPO .

OTHER PUBLICATIONS

Boss et al, Nucleic Acids Research 12 (9):3791–3806, 1984.

Georgiou et al., Trends in Biotechnology 11(1):6–10, Jan. 1993.

Georgiou et al., "Practical Applications of Engineering Gram–Negative Bacterial Cell Surfaces," *Tibtech,* vol. 11, pp. 6–10 (1993).

Laukkanen et al., "Lipid–tagged Antibodies," *Protein Engineering,* vol. 6, No. 4, pp. 449–454 (1993).

Biological Abstracts, vol. 88, No. 084626 (1989).

Gbrayeb et al., The Journal of Biological Chemistry, vol. 269, pp. 463–467 (Jan. 1984).

Francisco et al., Proc. Natl. Acad. Sci. USA, vol. 89, pp. 2713–2717 (Apr. 1992).

*Primary Examiner*—Paula K. Hutzell
*Assistant Examiner*—Eliane Lazar-Wesley
*Attorney, Agent, or Firm*—Birch, Stewart, Kolasch & Birch, LLP

[57] ABSTRACT

A recombinant vector for cloning a heterologous nucleotide sequence and/or expressing it and/or transferring it to a cell host. The vector includes, at a site which is not essential for replication, the gene coding for a lipoprotein other than *E. coli* lipoproteins, or a part of said gene which contains the elements required for controlling the expression of said lipoprotein and exposing it on the surface of the outer host cell membrane, so that the heterologous nucleotide sequence can be inserted into the gene or said part thereof under conditions suitable for expressing said heterologous sequence and exposing it on the surface of the cell host.

23 Claims, 35 Drawing Sheets

CCGGGAAATTGCTTACTTGCGCCGCACGCTGGATATTTTTTGAACAAACGA -158
CACTCCAACTACTGCTAAAGTCGGGGGGACTAAAAAAAAAGTTGCTCGGCT -107
TGCGCTTGGTCAGTTTACTTACTACAAGTAATGGGTAGTATGTAGCCGGCT -56
AATTTCCCCGGCTGGAGATTGCTGTTATGGAAATGTCCACCTTAAGGGGAA -5
CACG   1 ATG AAC AAC GTT CTG AAA TTC TCT GCT 27
         Met Asn Asn Val Leu Lys Phe Ser Ala
CTG GCT CTG GCT GCT GTT CTG GCC ACC GGT TGC AGC AGC 66
Leu Ala Leu Ala Ala Val Leu Ala Thr Gly Cys Ser Ser
CAC TCC AAA GAA ACC GAA GCT CGT CTG ACC GCT ACC GAA 105
His Ser Lys Glu Thr Glu Ala Arg Leu Thr Ala Thr Glu
GAC GCA GCT GCT CGT GCT CAG GCT CGC GCT GAC GAA GCC 144
Asp Ala Ala Ala Arg Ala Gln Ala Arg Ala Asp Glu Ala
TAT CGC AAG GCT GAC GAA GCT CTG GGC GCT GCT GAG AAA 183
Tyr Arg Lys Ala Asp Glu Ala Leu Gly Ala Ala Gln Lys
GCT CAG CAG ACC GCT GAC GAG GCT AAC GAG CGT GCC CTG 222
Ala Gln Gln Thr Ala Asp Glu Ala Asn Glu Arg Ala Leu
CGC ATG CTG GAA AAA GCC AGC CGC AAG TAA TAG GTCTCAC 262
Arg Met Leu Glu Lys Ala Ser Arg Lys Stop Stop
GACCCTGTTGAAAACCGGTCCCTCGGGGCCGTTTTTTATGCCTGCGTTTCG 313
CCGGGCATGAAAAAACCCGCGTCCCTTG                         341

*Fig. 3*

```
         SphI      HpaI    EcoRI        BglII       SphI
5'___CGC ATG CGG TAA ACA GAA TTC TCA GAG ATC TGC ATG CTG GAA 3'___
     gln met arg leu thr glu phe ser glu ile cys met leu glu
```

Lpp35

```
              BglII
   SphI                EcoRI      HpaI       SphI
5'___CGC ATG CAG ATC TCT GAG AAT TCT GTT AAC CGC ATG CTG GAA 3'___
     gln met gln ile ser glu asn ser val asn arg met leu glu
```

Lpp36

*Fig. 8A*

```
5'                                                                          3'
AA TTC AAC ATC GCT CAC ATC TCT  TCT  TCT  TCT GCT  CGT ACT GGT GAC G
    Phe Asn Ile Ala His Ile Ser  Ser  Ser  Ser Ala Arg Thr Gly Asp
      G  TTC TAG CGA GTG TAG AGA AGA AGA AGA CGA GCA TGA CCA CTG CTTAA
3'                                                                          5'
```

Fig. 8B

λgt11

RECOMBINANT VECTOR CONTAINING A SEQUENCE OF A LIPOPROTEIN GENE FOR THE EXPRESSION OF NUCLEOTIDE SEQUENCES

The invention relates to a recombinant vector containing a sequence of a structural lipoprotein gene for the expression of nucleotide sequences.

One of the aims of the invention is to propose new means for preparing, by genetic engineering techniques, proteins, polypeptides or peptides, in the form of products (optionally of fusion products) capable of being exposed at the level of the external membrane of the cell which produces them. In other words, the invention provides vectors for the expression, by recombinant cells, of extracellular proteins anchored in the membrane of these cells.

There are known in the state of the art various vectors which make it possible to express, in recombinant cell hosts, amino acid sequences and which allow, where appropriate, the exposure of these proteins at the surface of the cell host. Plasmids or phages have for example been used in the state of the art to express polypeptide in Gram-negative bacteria and to expose them at their surface.

Thus, Francisco J. A. et al. (Bio/Technology vol. 11, April 1993, p. 491–495) have expressed in E. coli an exoglucanase in the form of a hybrid protein (fusion protein) with the transmembrane domain of the OmpA protein naturally contained in the external membrane of E. coli, itself fused with the first nine amino acids of the E. coli major lipoprotein (also called Braun's lipoprotein (Lpp), expressed at the level of the external membrane). According to Francisco et al., the fusion protein thus obtained is anchored at the surface of the external membrane of E. coli.

Francisco et al. used a fusion product involving the OMPA protein which allows, within this hybrid construct, the exposure of exoglucanase at the surface of E. coli.

Other authors, Fuchs P. et al. (Bio/Technology Vol. 9, December 1991, p. 1369–1372) have described the expression, in E. coli, of a fusion protein formed by the variable domains of the heavy chains and light chains of antibodies, fused with the peptidoglycan-associated lipoprotein (PAL) of E. coli. In order to obtain a fusion protein which is accessible at the surface of E. coli cells, a sequence for the export of a pectin lyase was used and the N-terminal cysteine of PAL was converted to glycine, thus preventing the attachment of the lipids of lipids of the external cell membrane to the cysteine normally present in PAL.

The lipoproteins used by Fuchs et al. according to the abovementioned publication are lipoproteins belonging to the cytoplasmic membrane of the cell.

The inventors of the present application focused their attention on other lipoproteins, especially on structural lipoproteins analogous to the E. coli Braun's lipoprotein insofar as they have the capacity to become attached to the external cell membrane, on the one hand, and in some cases to the peptidoglycans, on the other hand. These lipoproteins were used within the framework of the invention to prepare recombinant vectors intended especially for the expression and export, at the surface of the external membrane of recombinant cells, of amino acid sequences.

Preferably, the lipoprotein used is not an E. coli lipoprotein.

The subject of the invention is a recombinant vector for the cloning and/or expression and/or transfer, into a cell host, of a heterologous nucleotide sequence, characterized in that it comprises, at a site not essential for its replication, the gene encoding a lipoprotein different from the E. coli lipoproteins, or part of this gene which contains the components necessary for controlling the expression of this lipoprotein and for its exposure at the surface of the external cell membrane of the host, such that the heterologous nucleotide sequence is capable of being introduced into the gene or the part of the gene encoding the lipoprotein, under conditions allowing the expression of this heterologous sequence and the exposure of the polypeptide obtained at the surface of the cell host.

The expression "heterologous nucleotide sequence" is understood to mean any nucleotide sequence which is not naturally contained in the nonrecombined vector used to prepare the vectors of the invention.

The size of the nucleotide sequence may vary considerably, from a few nucleotides (for example 9) to several hundreds of nucleotides, for example up to 1 kb or 2 kb.

In other words, the nucleotide sequence contained in the vector may encode proteins having a molecular weight which may be as high as about a hundred kilodaltons.

The heterologous nucleotide sequence is preferably introduced at the level of the N-terminal part of the mature Lpp protein, for example 3 to 4 amino acids following the N-terminal end.

Preferably, the structural lipoprotein in question above is a structural lipoprotein of a bacterium.

The recombinant vector of the invention contains a lipoprotein termed structural lipoprotein, as opposed to the E. coli PAL lipoprotein.

Preferably, it is a lipoprotein of a Gram-negative bacterium.

The gene encoding this lipoprotein is preferably introduced in its entirety into the vector. However, there may also be used only one or more parts of this gene provided that the components necessary for controlling the expression of the lipoprotein and for its exposure at the surface of the external cell membrane of the host cell modified by the vector of the invention are present in the construct. In particular, a part of the gene encoding a lipoprotein which contains what is called the "lipoprotein box" (Milton J. et al., CRC Press (1993) International Standard Book Number 0-8493-6740-9, Chapter 6, p. 163–181) will be used. This region corresponds to a carboxy-terminal region present in the signal sequence of the lipoprotein.

The gene or the part of the gene encoding a lipoprotein is introduced into the vector of the invention such that this gene or this gene part may, in addition, contain a heterologous nucleotide sequence present in the lipoprotein such that it is expressed and exposed at the surface of the cell membrane of a host into which the recombinant vector will have been previously introduced.

According to a first embodiment of the invention, the recombinant vector is characterized in that the gene encoding the structural lipoprotein or part of this gene is modified by inserting a heterologous nucleotide sequence.

This insertion can therefore be carried out after introducing the lipoprotein gene or part of this gene into a given vector.

It is also possible, according to another variant embodiment, to introduce a heterologous nucleotide sequence into the lipoprotein gene or part of this gene and then to introduce this recombinant sequence into the vector chosen to construct a recombinant vector according to the invention.

Advantageously, the recombinant vector is a plasmid.

According to a first variant embodiment of the invention, the lipoprotein whose gene or gene part is used is a heterologous protein in relation to the cell host containing the vector.

In other words, this specific lipoprotein is not naturally present in the cell host chosen for the expression and/or cloning of the recombinant vector of the invention. It is, however, not excluded that the chosen cell host expresses another lipoprotein naturally.

Preferably, the gene encoding the lipoprotien or part of this gene used to prepare the vector of the invention is the gene encoding the major lipoprotein of the external membrane of a bacterium of the genus Pseudomonas. Preferably, the bacterium is a bacterium of the *Pseudomonas aeruginosa* type.

Other lipoproteins can also be used and in this regard, there may be mentioned the Braun lipoproteins and in particular that of *S. marcescens* (Nakamurak et al. PNAS, USA 77 (1980) 1369), *E. amylovora* (Yamagata H. et al., J. Biol. Chem., 256—(1981) 2194), *M. morganii* (Huang Y. X. et al., J. Biol. Chem., 258 (1983) 8139), *P. mirabilis* (Ching G. et al., J. Biol. Chem., 261 (1986) 4600); they may also be other proteins of Gram-negative bacteria and in particular the following: Pullulanase of *K. pneumoniae* (Chapon C. et al., "Structure of two divergent promoters in front of the gene encoding pullulanase in *Klebsiella pneumoniae* and positively regulated", J. Bacteriol., 164 (1985) 639), *K. aerogenes* (Katsuragi N. et al., "Entire nucleotide sequence of pullulanase gene of *K. aerogenes* WVO", J. Bacteriol., 169 (1987) 2301), Pul S of *K. pneumoniae* (d'Enfert C. et al., "*K. pneumoniae* puIS gene encodes an outer membrane lipoprotein required for pullulanase secretion", J. Bacteriol., 171 (1989) 3673), chitobiase of *V. harveyi* (Soto-Gil R. et al. "Diacetylchitobiase of *V. harveyi*", J. Biol. Chem., 264 (1989) 14778), β-1,4-endoglucanase of *P. solanacearum* (Huang J. et al. "Excretion of the eft gene product of *P. solanacearum*", J. Bacteriol., 171 (1989) 3767), Pal and Pcp of *H. influenzae* (Deich R. "Cloning of genes encoding a 15,000-Dalton peptidoglycan-associated outer membrane lipoprotein and an antigenically related 15,000-Dalton protein from *H. influenzae*", J. Bacteriol., 170 (1988) 489), cytochrome subunit from *Rps. viridis* (Weyer K., "The cytochrome subunit of the photosynthetic reaction center from *Rps. viridis* is a lipoprotein", Biochemistry, 26 (1987) 2909).

In order to facilitate the insertion or the control of the insertion of the heterologous nucleotide sequence into the lipoprotein gene or gene part, one or more restriction sites can be introduced into this gene or this gene part, by means of for example a polylinker.

Preferably, the restriction sites for the polylinker are unique in relation to the sites present naturally in the vector before recombination and in relation to the sites present in the gene or the gene part encoding the lipoprotein.

Depending on the nature of the vector chosen to prepare the recombinant vector of the invention and in particular of the promoter controlling the expression of the sequence, the expression of the heterologous nucleotide sequence may be constitutive or, on the contrary, inducible, for example by metals and especially by zinc or by inducers such as IPTG.

Furthermore, a vector according to the invention may be present in the recombinant cells permanently or transiently. In this regard, the heterologous sequence may be maintained in the host cell by means of the vector of the invention, in the form of a plasmid. It may, according to one variant, be on the contrary integrated into the chromosomes of the host cell.

The subject of the present application is in particular the plasmid pLPI34 deposited at the BCCM (Belgian Coordinated Collections of Microorganisms) at LMBP (Laboratorium voor Moleculaire Biologie-Plasmidencollectie) on Jul. 27, 1993 under the No. LMBP2916.

Other vectors which are particularly preferred for carrying out the invention are the vectors pLPI35 and pLPI36 which are modified in relation to the vectors pLPI34, by the insertion of a polylinker.

Other particularly preferred vectors are the vectors pVUB-1 and pVUB-2.

The recombinant vector according to the invention constitutes a means for preparing, in a cell host, antigens or, more generally, amino acid sequences of any origin or of any structure or function.

The capacity of the recombinant vector of the invention to express, in a form exposed at the external cell membrane of the host cell, the amino acid sequence encoded by the heterologous nucleotide sequence makes it possible easily to purify the amino acid sequence thus obtained. Moreover, it is possible to use directly the recombinant cells, especially the recombinant bacteria, expressing at their surface the amino acid sequence encoded by the heterologous sequence, without resorting to prior lysis of the host cells. This is especially advantageous in the case where the host cells are used in live vaccines.

In particular, the recombinant vector of the invention may be used to express amino acid sequences containing one or more antigenic determinants or one or more haptens.

In general, such a vector allows the expression of any peptide, polypeptide or of any recombinant protein. This peptide, polypeptide or this protein will be expressed in the form of a fusion product with the lipoprotein or part of the lipoprotein whose coding sequence is present in the recombinant vector.

Advantageously, the recombinant vector of the invention can be used to express a heterologous nucleotide sequence encoding a T type epitope of a determined antigen of a pathogenic agent. These pathogenic agents may be bacteria, viruses, parasites or, advantageously, any agent against which a vaccinal or therapeutic activity is sought.

Advantageously, the heterologous nucleotide sequence contained in the vector encodes a T epitope of a given antigen and a B epitope of this same antigen or of another antigen of a pathogenic organism against which immunization is sought.

From the point of view of one of the applications of the invention, that is to say the preparation of immunogenic compositions, the fusion peptides, polypeptides or proteins (more generally called fusion proteins) contain one or more antigens and/or one or more antigenic determinants of a pathogenic agent such as a parasite, a bacterium or a virus, for example, especially a virus such as that of hepatitis A, B or C, an HIV virus and for example HIV envelope antigens.

Nonlimiting examples are given in the experimental part which follows.

According to another specific embodiment of the invention, the vector contains a heterologous nucleotide sequence encoding an amino acid sequence of an antibody. Such a sequence may be an amino acid sequence of a heavy chain or of a light chain of an antibody with 4 chains or advantageously a sequence encoding a nonpathological antibody consisting exclusively of heavy chains. In this regard, reference may be made to the publication by Hamers et al., Nature, Vol. 363, Jun. 3, 1993, p. 446–448 which describes the production and the characterization of such antibodies.

The subject of the invention is also a recombinant host cell, characterized in that it is modified by a recombinant vector according to the invention. According to an advantageous embodiment of the invention, this host cell does not express naturally the lipoprotein encoded by the gene or the gene part contained in the vector.

Such a host cell is for example a Gram-negative bacterium and especially a strain of *E. coli* or a strain of *Alcaligenes eutrophus*.

The vector modified by nucleotide sequences encoding an antibody may be for example introduced into a host cell, especially into a bacterium which is then capable of producing antibodies exposed at the surface of the host, it being thus possible for the said recombinant cells to be used for example as adsorbent for the purification of antigens.

The subject of the invention is also a recombinant protein, characterized in that it is the product of expression, by a cell host defined above, of the gene or part of the gene for a lipoprotein and of a heterologous nucleotide sequence.

A recombinant protein of the invention is a protein from the fusion between a lipoprotein chosen from the lipoproteins different from those of *E. coli* and/or part of such a lipoprotein and a determined amino acid sequence.

This recombinant protein, when it contains one or more antigenic determinants, has the property of allowing, in vivo, the production of antibodies directed against the antigenic determinant encoded by the heterologous nucleotide sequence defined above, without this production being disrupted by the presence of the carrier molecule, in this case the lipoprotein.

In addition, the results obtained demonstrate that the fusion protein produced allows, in vivo, the production of antibodies against the antigen encoded by the heterologous sequence without the need to add an adjuvant to the composition administered.

The subject of the invention is therefore immunogenic compositions comprising, as active ingredient, recombinant proteins as defined above, carrying one or more antigenic determinants against which it is desired to obtain antibodies.

Other immunogenic compositions comprise the recombinant cell hosts of the invention.

The invention relates moreover to polyclonal or monoclonal antibodies, characterized in that they recognize a recombinant protein or fusion polypeptide of the invention, comprising, on the one hand, the sequence encoded by the lipoprotein gene or gene part and, on the other hand, the amino acid sequence encoded by the heterologous nucleotide sequence.

Specific monoclonal antibodies according to the invention are in particular characterized in that they recognize the sequence encoded by the lipoprotein gene or gene part and in that they do not recognize the fusion polypeptide defined above, comprising, on the one hand, the sequence encoded by the lipoprotein gene or gene part and, on the other hand, the amino acid sequence encoded by the heterologous nucleotide sequence.

A particularly advantageous antibody is the KF9 antibody produced by the KF9 hybridoma deposited at ECACC (European Collection of Animal Cell Cultures Salisbury, United Kingdom) under the No. 93073008 on Jul. 30, 1993. This antibody has the extremely valuable advantage of recognizing the lipoprotein expressed by the vector and of not recognizing this lipoprotein or part of this lipoprotein when it is modified by an insert corresponding to a heterologous nucleotide sequence having a size greater than that of a polylinker. Thus, this antibody may for example be used to screen for the expression of the fusion polypeptides of the invention.

Other characteristics and advantages of the invention appear in the examples and the figures which follow.

FIG. 1: Construction of the vectors pLPI35 and pLPI36.

pLPI35 and pLPI36 are low copy number vectors which allow the constitutive expression of the lipoprotein whose coding sequence has been modified by the addition of a polylinker to its reading frame.

The plasmid pLPI1 is derived from the vector pKT240. It contains a SalI fragment of the *P. aeruginosa* lipoprotein having a size of 2.94 kb, cloned into the XhoI site of the vector.

Stage 1 of the construction starts with the original plasmid pLPI1 which was cut with SstI and digested with Bal31 in order to remove gradually DNA in both directions starting from the SstI site (according to the conditions described in "Molecular Cloning—A laboratory manual second edition"—Sambrook et al. (1989).

A clone still producing the *P. aeruginosa* lipoprotein was selected by positive reaction with an antilipoprotein monoclonal antiserum.

The map of the plasmid obtained, pLPI34, is represented. pLPI34 lost 2 kb of DNA and the following restriction sites: EcoRI, HpaI, NruI, SphI (2x), SstII, SstI. The plasmid pLPI34 contains a unique site for SphI toward the end of the reading frame of the lipoprotein gene (OprI).

Stage 2 consists in a cloning of a polylinker with SphI cohesive ends containing the sites HpaI (blunt ends), EcoRI and BglII. The plasmids pLPI35 and pLPI36 contain the polylinker in both directions. The polylinker was designed so as not to interrupt the reading frame, regardless of the orientation of the insert.

These two plasmids allow the insertion of DNA fragments cut with the following enzymes: BglII, BamHI, Sau3A and MboI (in the BglII site), EcoRI and any fragment with straight ends (in the HpaI site). They are in a low copy number (4 to 5) and are conjugative, that is to say that they can be transferred by conjugation to other Gram-negative bacteria. The expression of the lipoprotein is constitutive in these vectors.

A monoclonal antibody, KF9, still recognizes the lipoprotein produced by pLPI36 but no longer reacts when a fragment was inserted into one of the cloning sites mentioned above.

The expression of the proteins from the fusion between the lipoprotein and the insert is constitutive by virtue of the lipoprotein's own promoter.

FIG. 2: Construction of the vectors pVUB-1 and pVUB-2.

The expression vector pKK233-2 (Pharmacia) was used: its EcoRI site was removed by restriction, and then filling with the Klenow fragment and ligation were performed.

The resulting plasmid pKK233* was then restricted with NcoI, treated with Klenow and ligated with a PCR amplified fragment corresponding to the entire ORF of the modified gene for the lipoprotein of pLPI35 or of pLPI36 (lpp35 and lpp36, see step 2). This gave the two vectors pVUB-1 and pVUB-2.

In these multicopy vectors, the expression of the lipoprotein is controlled by IPTG. In order to avoid expression before induction, it is preferable to carry out cultures in B+glucose medium or in M9+glucose medium.

Figure 2A:
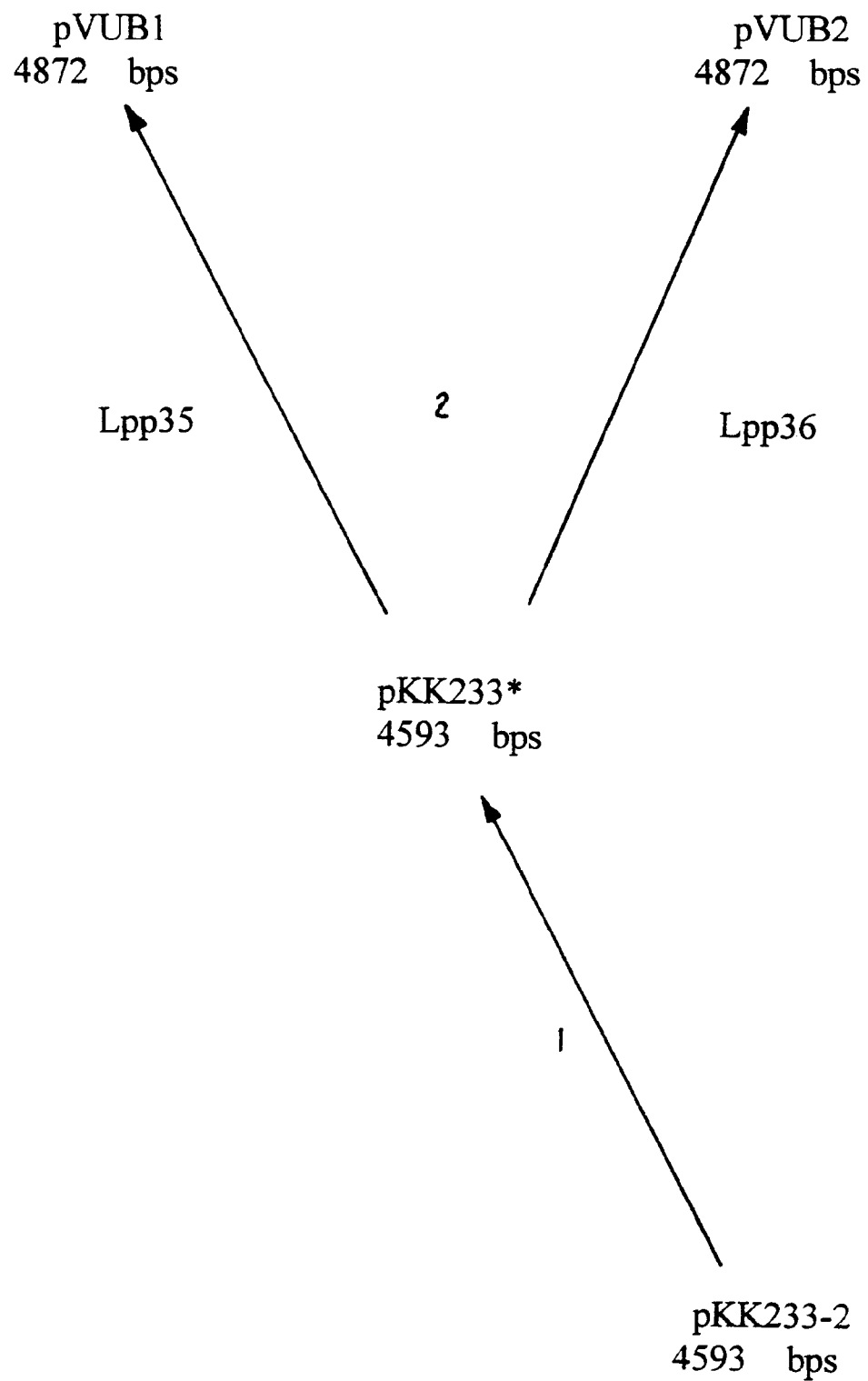
Figure 2B:
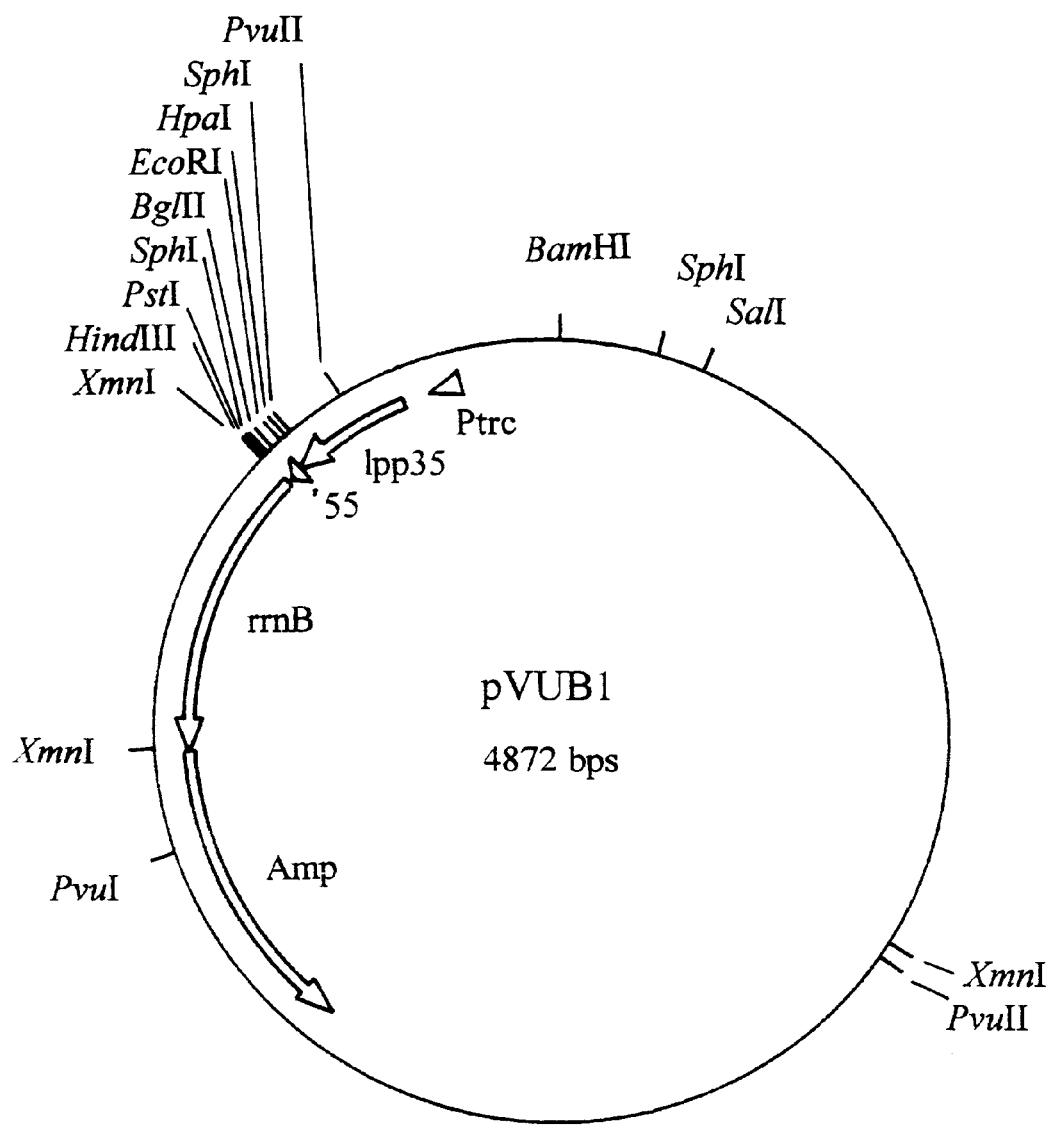
Figure 2C:
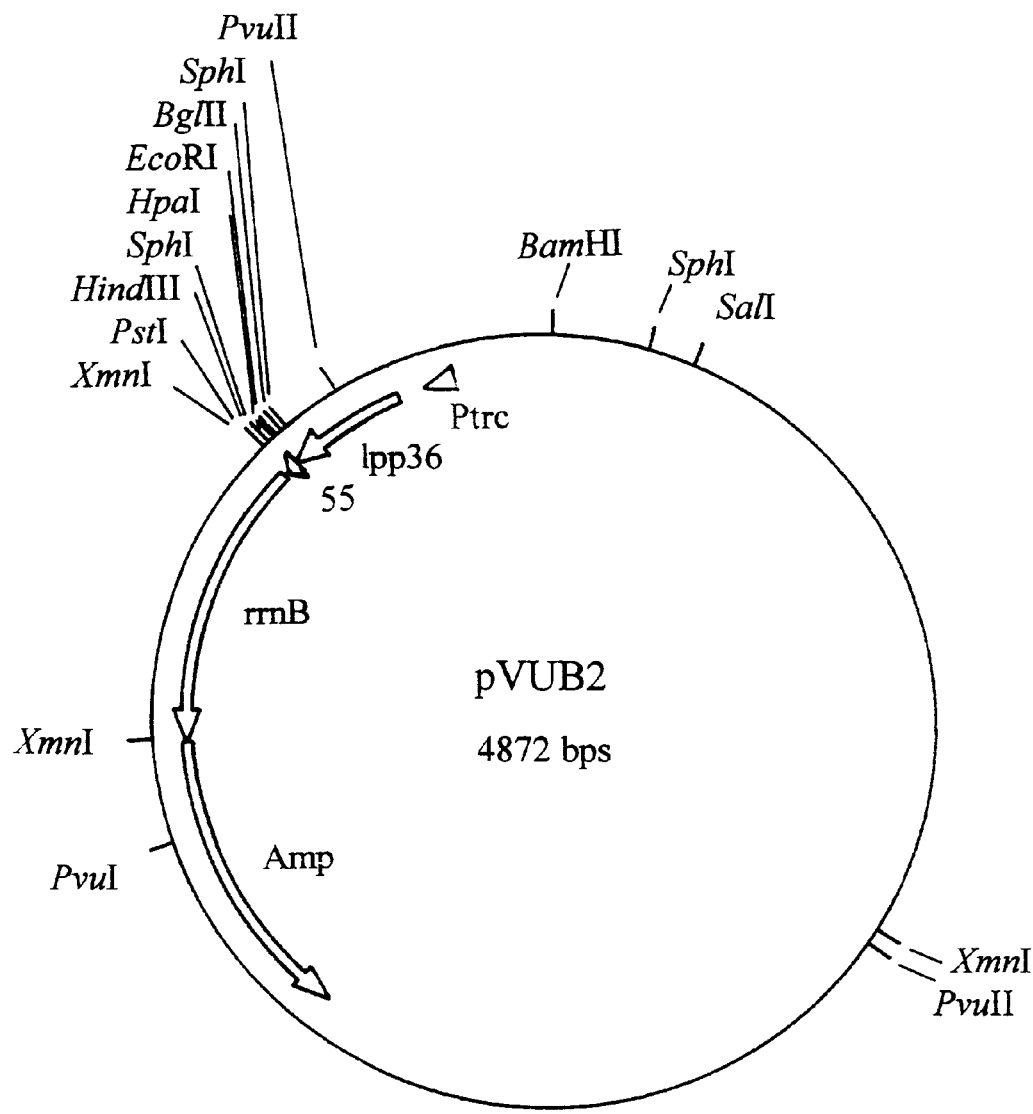
Figure 2D:
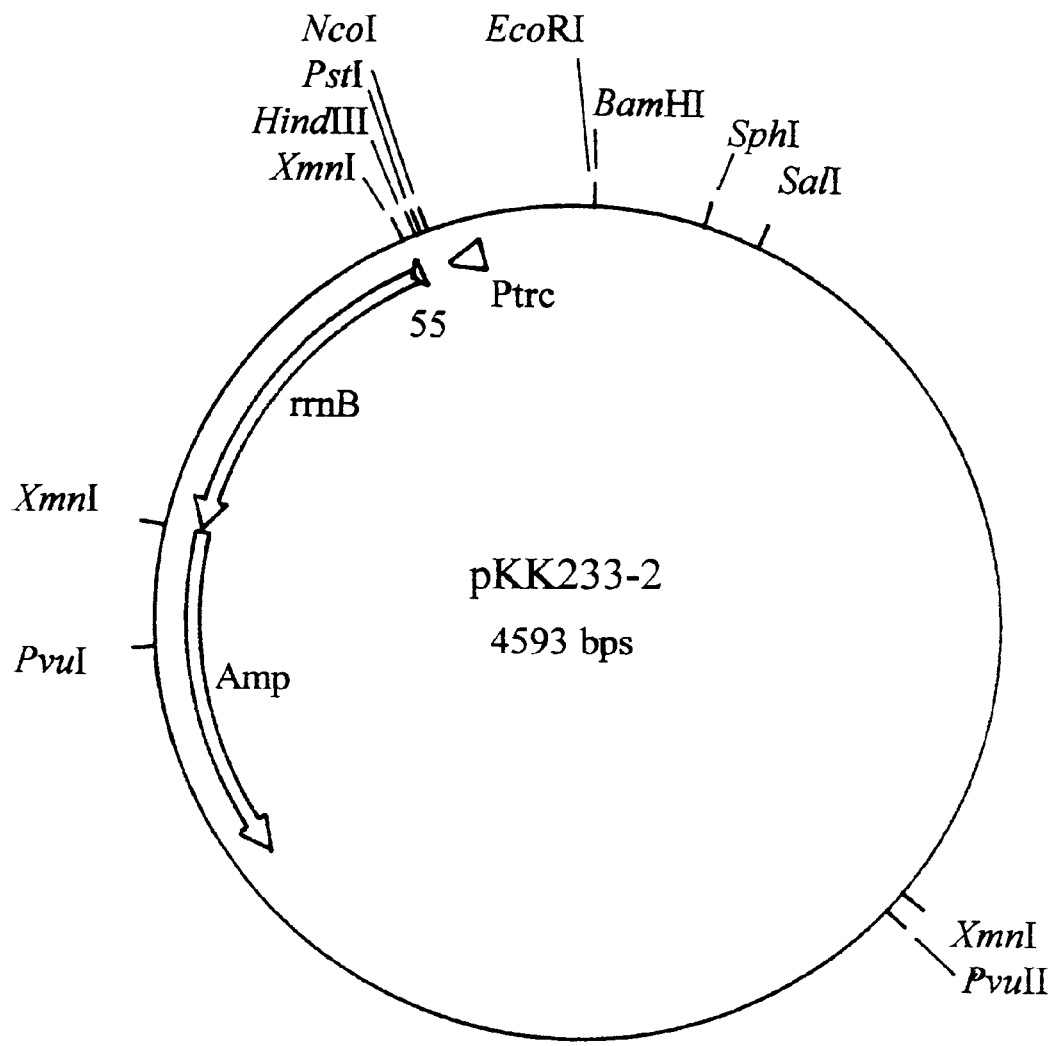
Figure 2E:
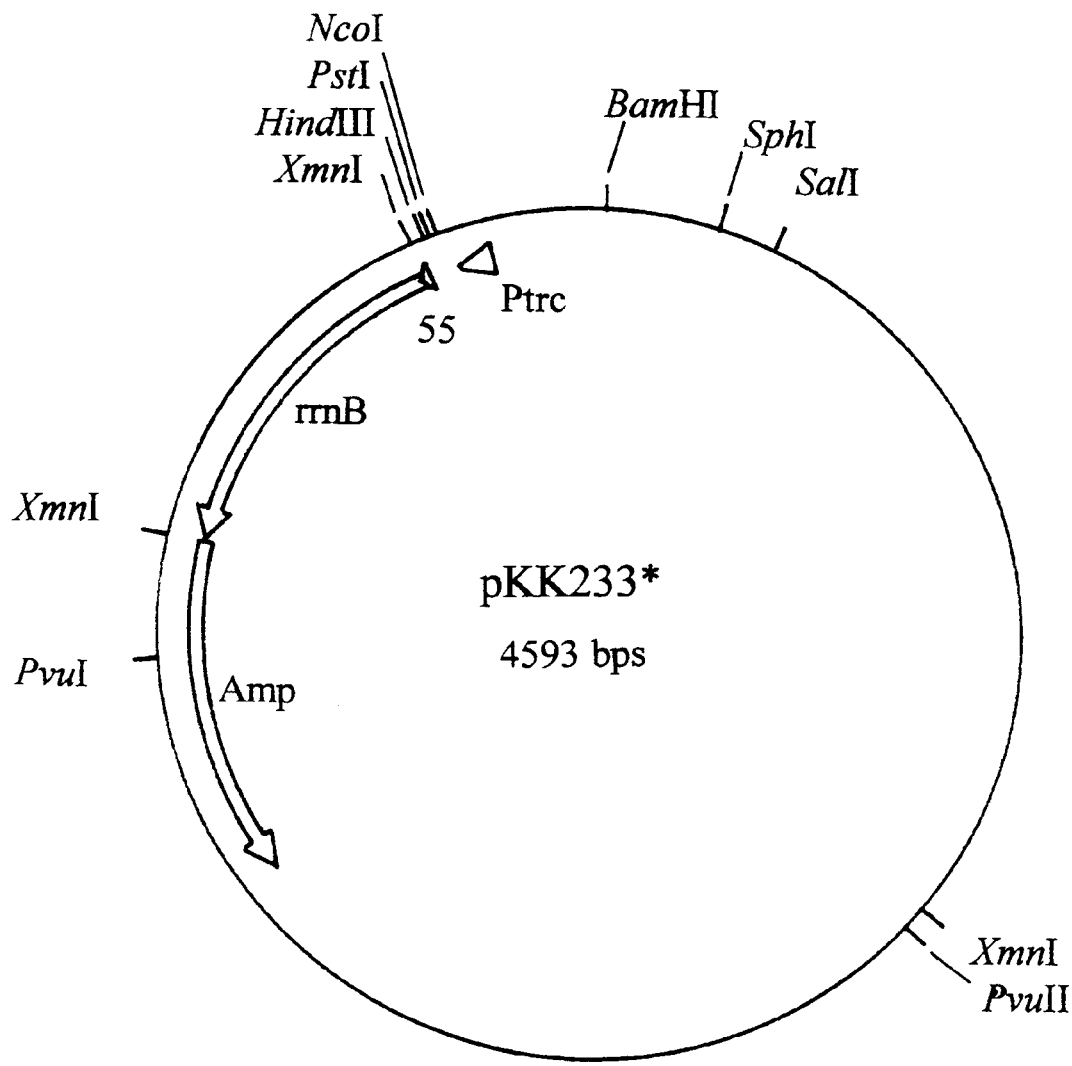
Figure 2F:
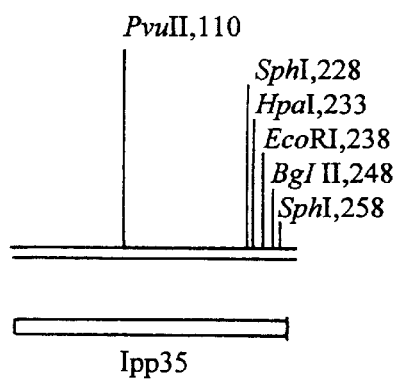
Figure 2G:
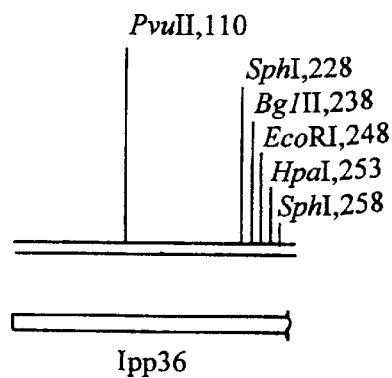

The sequences of the polylinkers used to construct the vectors pVUB1 and pVUB2 are given in FIGS. 2F and 2G.

FIG. 3: Coding sequence and corresponding amino acid sequence of the major lipoprotein of the membrane of *Pseudomonas aeruginosa*.

Figure 4A:
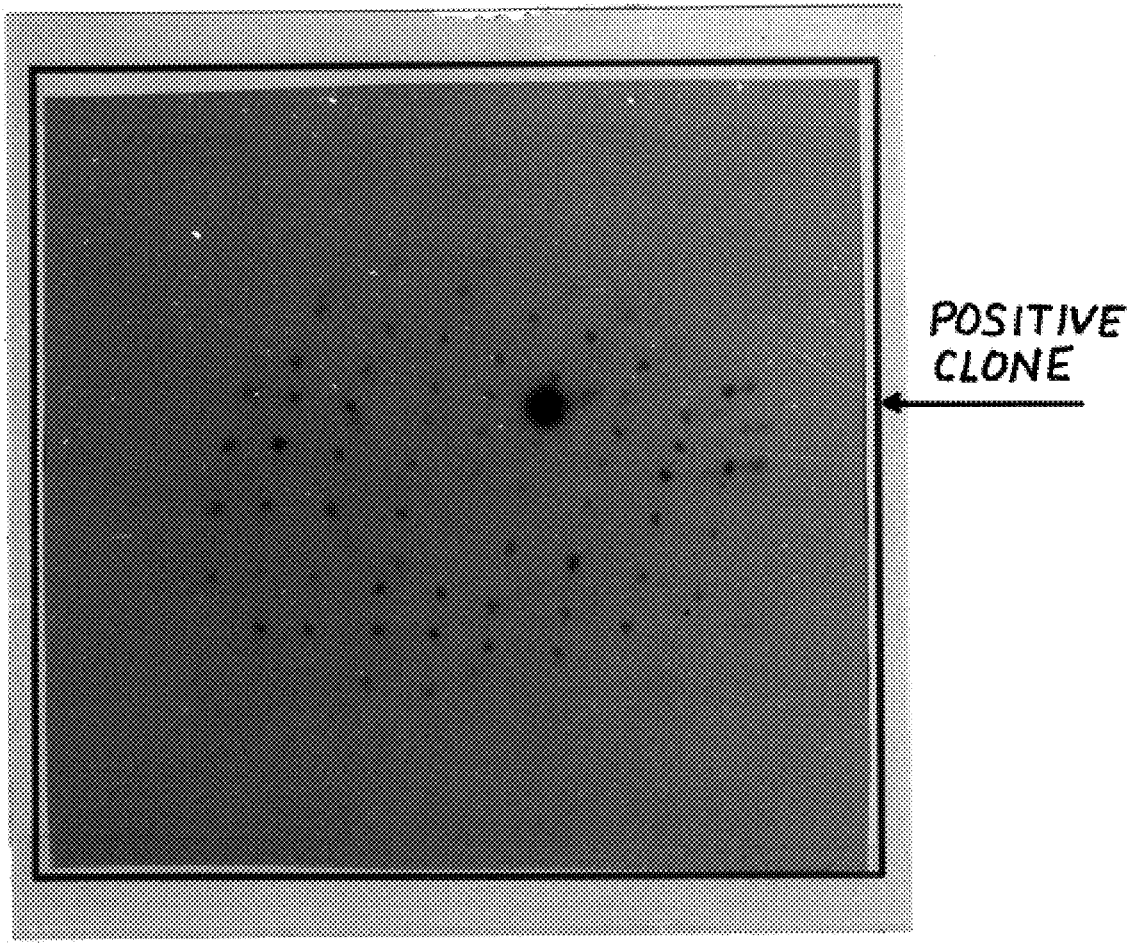
Figure 4B:

FIG. 4: (A) Recombinant *E. coli* JM 109 clones modified by the vector pVUB-1 containing a DNA fragment E.stR1 of an *Emeria stiedae* antigen. Detection of the positive clones by radioactive hybridization with the E.stR1 probe.

(B) Immunogold labeling and electron microscopy of *E. coli* JE5513 (lpp–) transformed with the plasmid pLPI34 containing the P. aeruginosa lipoprotein gene. The cells reacted with AcM FA2.5 and gold particles (10 nm) coupled with Protein A (magnification×45,000).

Figure 5:
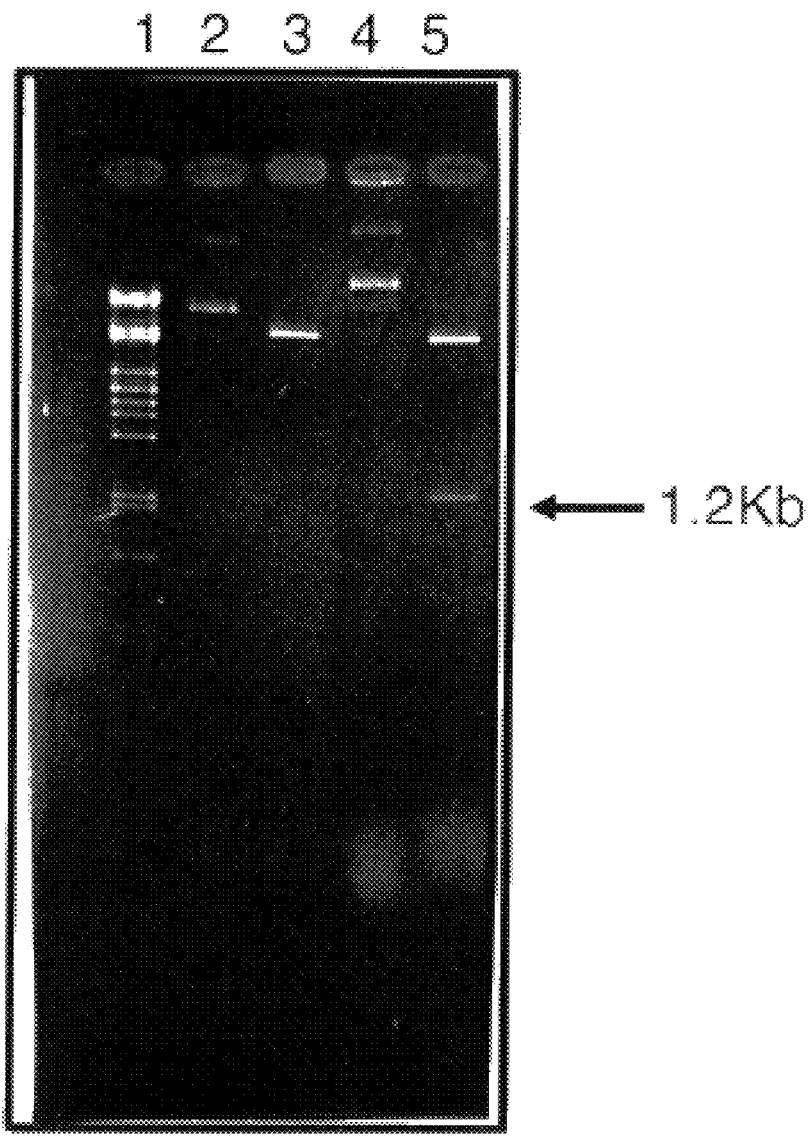

FIG. 5: DNA extracted from the recombinant E. coli JM 109 clone modified by the vector pVUB-1 containing the fragment E.stR1 of an E. stiedae antigen. Visualization on a 1–2% agarose gel of the extracted DNA.
1=λpst1 marker
2=pVUB.1 (undigested)
3=pVUB.1 (digested with EcoRI)
4=pVUB.1/E.stR1 (undigested)
5=pVUB.1/E.stR1 (digested with EcoRI)

Figure 6A:
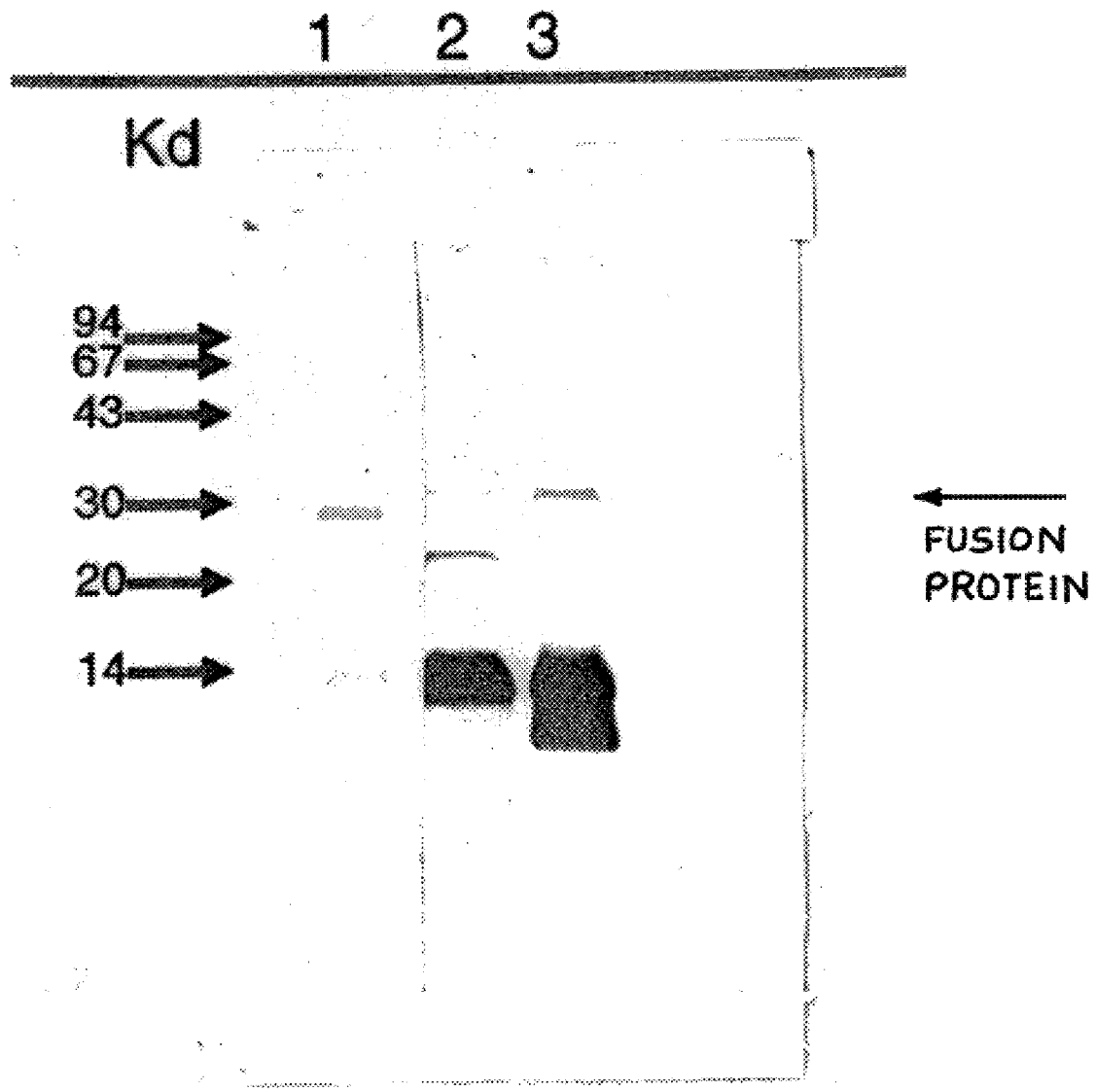
Figure 6B:
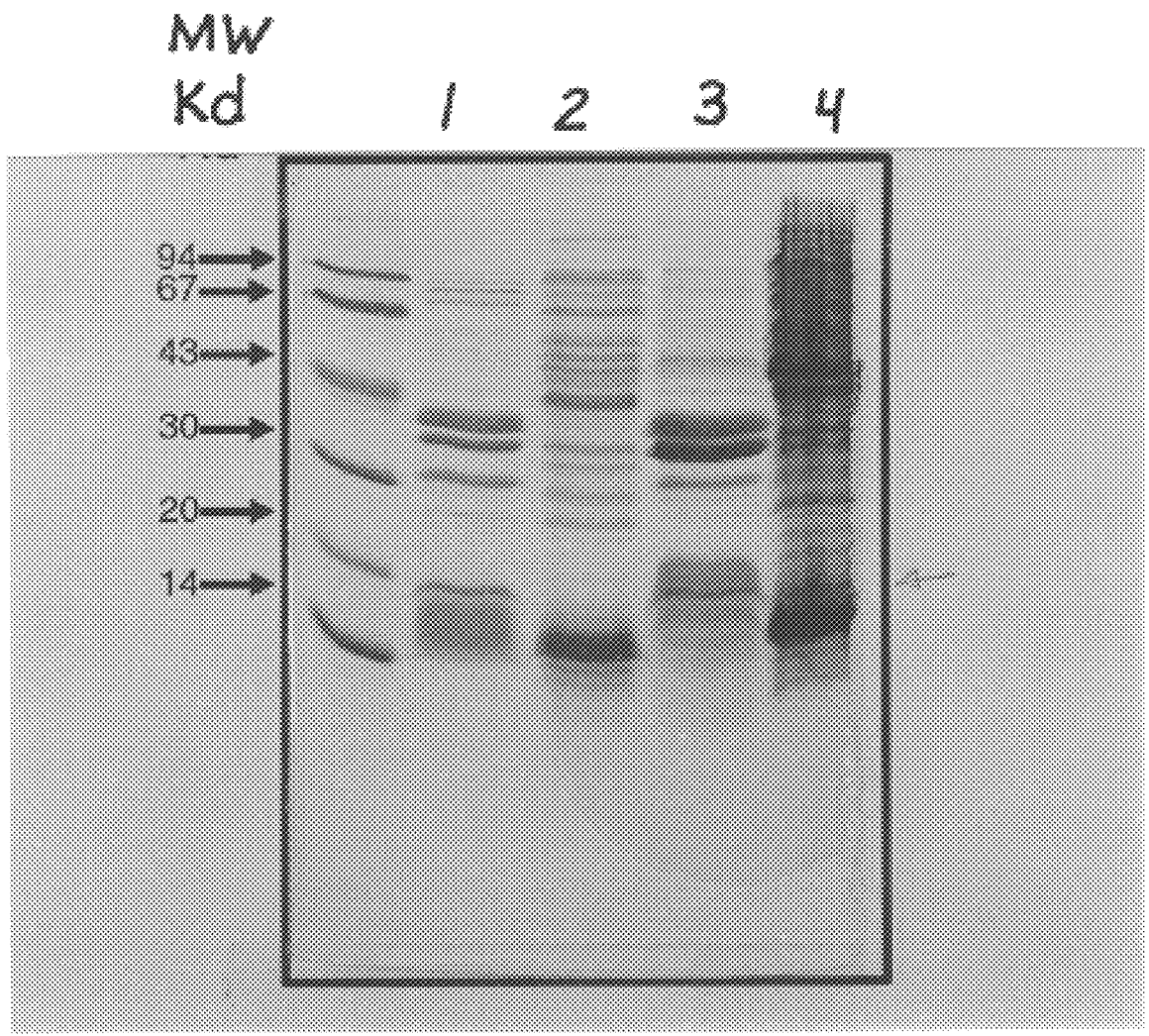
Figure 6C:
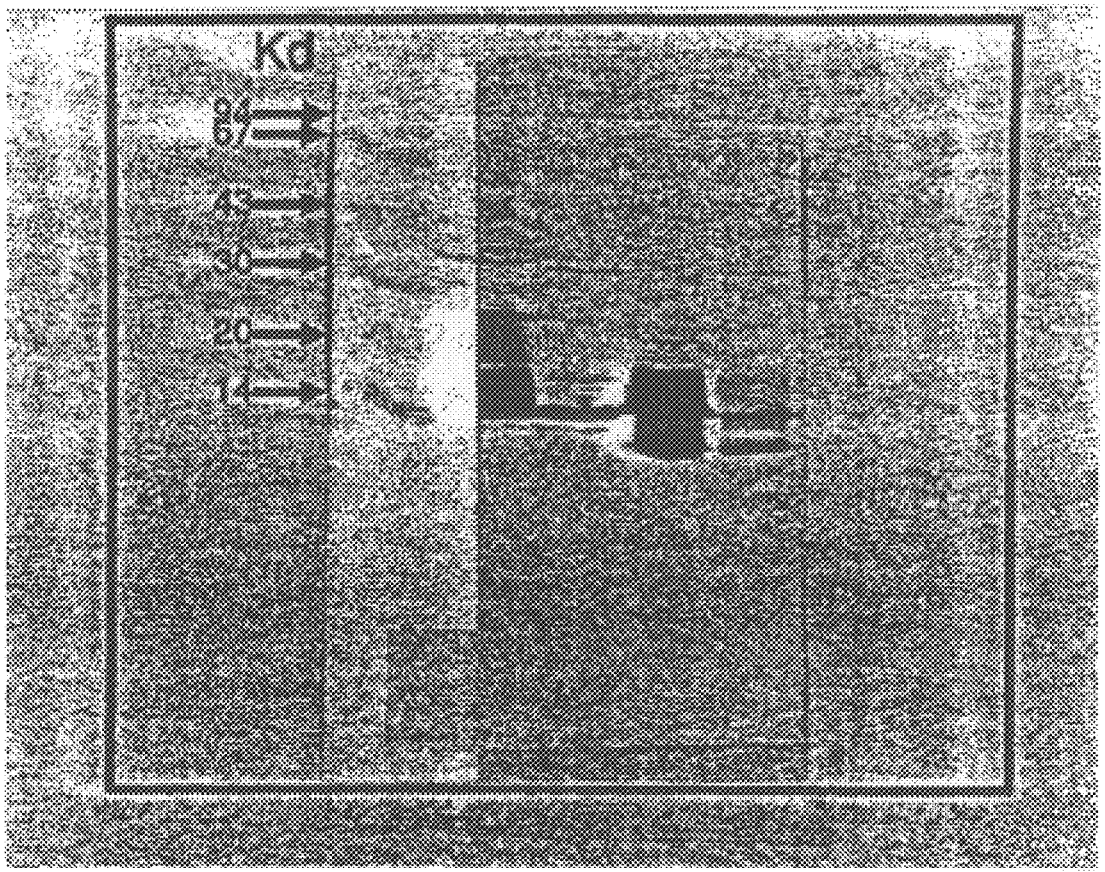
Figure 7A:
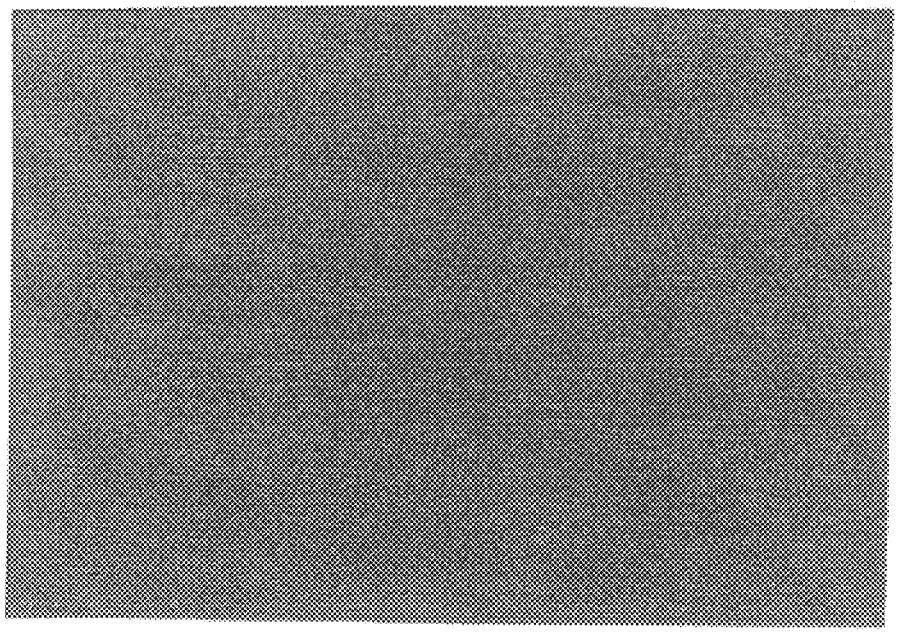
Figure 7B:
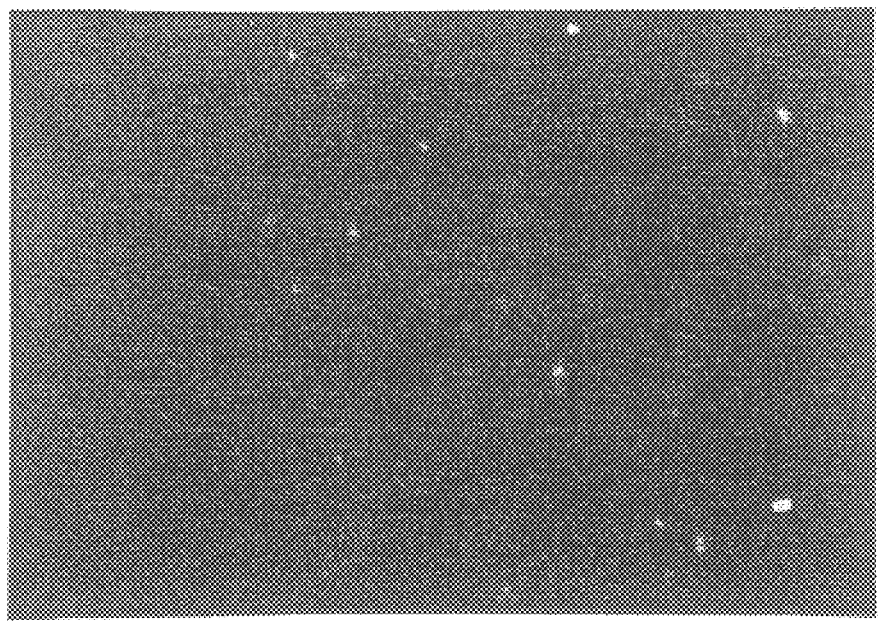
Figure 7C:
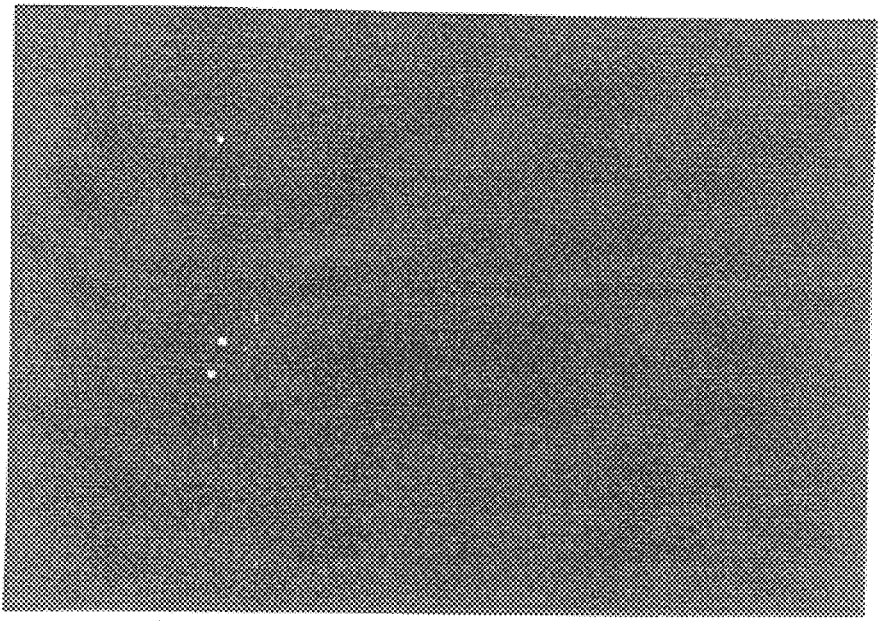
Figure 7D:
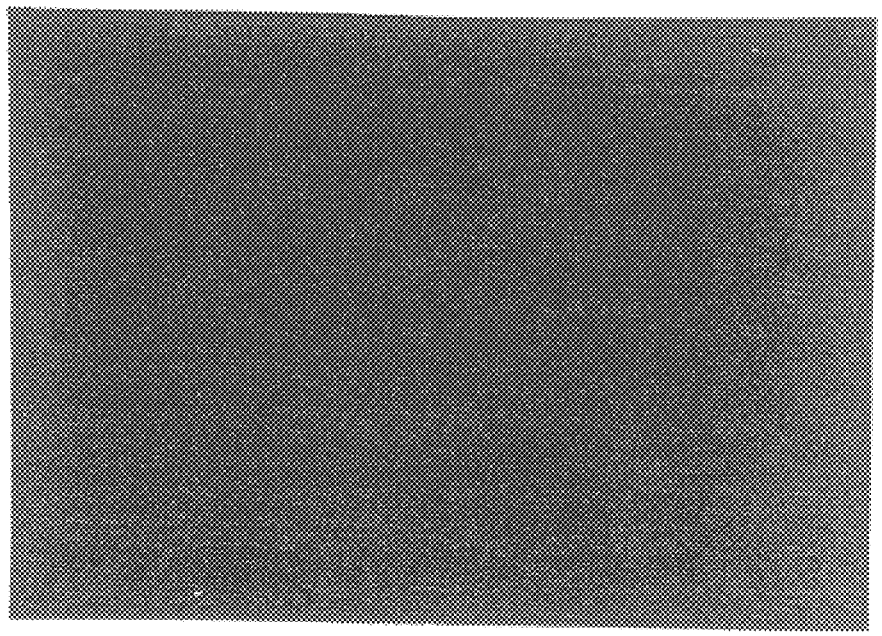
Figure 7E:
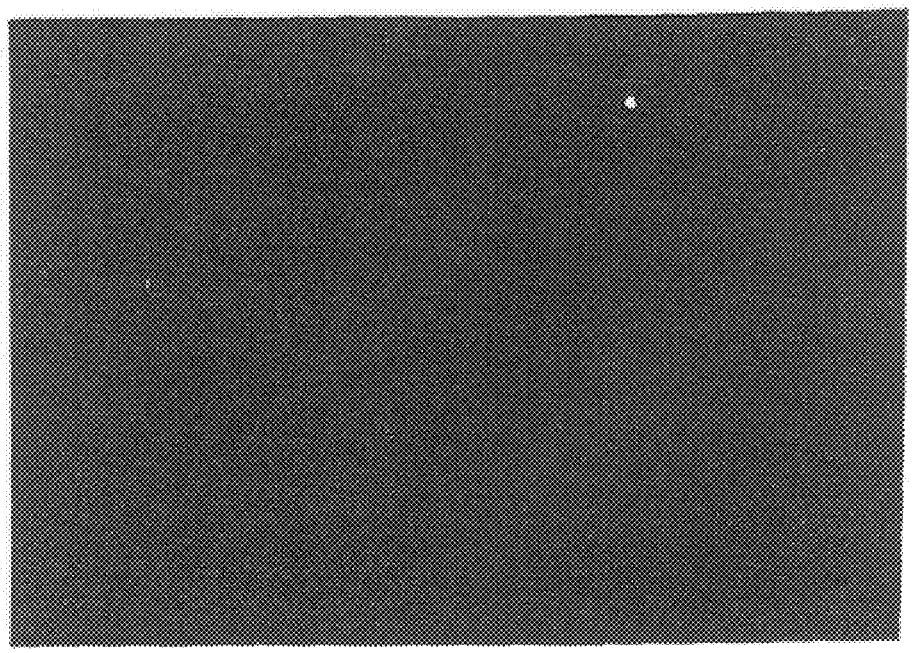
Figure 7F:
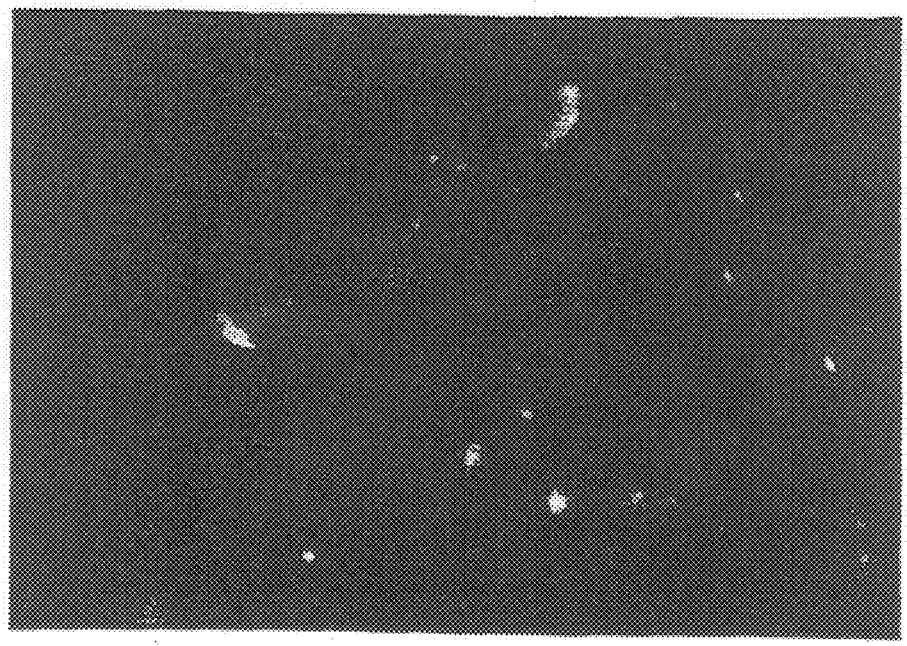

FIG. 6: (A) Western blot analysis for detecting the fusion protein; by reacting with an antibody FA 2.5 directed against the lipoprotein.
1=marker
2=pVUB-1
3=pVUB-1/E.stR1

(B) Separation on a 17.5% SDS-PAGE gel of the membrane and cytoplasmic fractions of the protein extracts of pVUB.1 and pVUB.1/E.stR1

| 1 = Membrane fraction<br>2 = Cytoplasmic fraction | pVUB.1 |
|---|---|
| 3 = Membrane fraction<br>4 = Cytoplasmic fraction | pVUB.1/E.stR1 |

(C) Western blotting of the membrane and cytoplasmic fractions of the protein extracts of pVUB.1 and pVUB.1/E.stR1: screening with the FA2.5 monoclonal (anti-lipoprotein)

| 1 = Membrane fraction<br>2 = Cytoplasmic fraction | pVUB.1 |
|---|---|
| 3 = Membrane fraction<br>4 = Cytoplasmic fraction | pVUB.35/E.stR1 |

FIG. 7: (A, B) Immunofluorescence with the anti-S2b rabbit serum previously adsorbed with E. coli JM109 transformed with the plasmid pLPI35.
(A) E. coli JM 109 with pLPI35
(B) Clone F3: E. coli JM 109 transformed with the fusion pLPI35-S2b. The S2b sequence contains epitopes T and B.
(C, D) Immunofluorescence with anti-S2b rabbit serum previously adsorbed with E. coli JM109 transformed with the plasmid pVUB1.
(C) E. coli JM 109 with pVUB1, not induced
(D) Clone F3: E. coli JM 109 transformed with the pVUB1 fusion, induced by IPTG.
(E, F) Immunofluorescence with anti-S2b rabbit serum previously adsorbed with E. coli JM109 transformed with the plasmid pVUB1.
(E) Clone D10=E. coli JM 109 with the pVUB1-S2b fusion, not induced;
(F) Clone D10=E. coli JM 109 transformed with the pVUB1-S2b fusion, induced with IPTG. The S2b sequence contains epitopes B and T.

FIG. 8: Insert encoding the S2b T epitope of hepatitis B cloned into the EcoRI site of the *P. aeruginosa* lpp.

Strategy for cloning the S2b T epitope into the vectors pVUB-1 and pVUB-2.

FIG. 9: Sequencing of the polylinker in the opposite orientation for pVUB-1 and pVUB-2. The restriction sites of the polylinker are indicated by the letters H=HpaI, E=EcoRI and B=BglII.

FIG. 10: Protein profile and production of the lipoprotein from the external membrane preparation, by coomassie blue staining (a, b and c) and by Western blotting (d and e) using the anti-lpp antibody FA 2.5.

FIG. 11: Primary structure of the PcLEMA gene; C43 and C159 are the cDNA fragments recognized by monoclonal antibodies; C159 is used to subclone into pVUB-1.

FIG. 12: Restriction map of the vector lambda gt11.

FIG. 13: Electrophoresis on a 0.8% agarose gel of plasmids digested with EcoRI: pVUB1 (lane 1), pVUB1-650 bp PcLEMA (lane 3), pVUB2 (lane 4), pVUB2-650 bp PcLEMA (lane 5) and PstI-digested lambda as standard marker (lane 1).

FIG. 14: Protein profile and production of Lpp from preparations of external membranes stained with coomassie blue (a, b, c) and by Western blotting, using the FA2.5 monoclonal antibody against Lpp. Preparation of external membranes (a) of pVUB1 (lanes 2, 3, 4 and 5) and pVUB2 (lanes 6, 7, 8 and 9); absence of induction, induction with IPTG for 1 h (lanes 3 and 7), 3 h (lanes 4 and 8), 6 h (lanes 5 and 9).

Preparation of external membranes of pVUB1 and pVUB2 (c); absence of induction (lane 2), induction by IPTG for 3 h with addition of $FeCl_3$ 5 $\mu$M (lane 3), 10 $\mu$M (lane 4), 25 $\mu$M (lane 5), 50 $\mu$M (lane 6) 100 $\mu$M (lane 7). Lane 1 corresponds to the standard marker.

FIG. 15: Western blot analysis of pLPI35 or of pVUB1 fused with Ag PcLEMA detected by the mAb FA2.5 directed against lpp (a) and the mAb32 against pcLEMA (b). Extraction of the total protein (a) in the absence of induction of pVUB1 (lane 2), pLPI 35-650 bp PcLEMA (lane 3), with IPTG induction of pVUB1-650 bp PcLEMA for 30 min (lane 4 and 7), for 3 h (lanes 5 and 8), 6 h (lane 6 and 9), induction with IPTG of pVUB1 for 3 h (lane 10).

Extraction of the total protein (b) in the absence of induction of pVUB1 (lane 2), with induction by IPTG induction of pVUB1 (lane 3), pLPI 35-650 bp PcLEMA (lane 4), with IPTG induction of pVUB1-650 bp PcLEMA for 30 min (lane 5), 3 h (lanes 6 and 7), 6 h (lane 7). Lane 1 corresponds to the standard marker.

FIG. 16: A. SDS-PAGE of the total protein of the external membrane.

1. pVUB2, induced for 5 hours
2. pC7 leishmania major gp63 gene cloned into pVUB2) induced for 5 hours B. Western blotting of the external membrane total protein tested with an anti-lipoprotein monoclonal antibody FA2.5.

1. pVUB2 after induction for 5 hours (the arrow indicates the modified lipoprotein.
2. pC7 after induction for 5 hours (the arrow indicates the fusion protein).

FIG. 17: Production of antibodies with the coccidiosis protein. The production of antibodies was tested after immunizing 4 groups of mice according to the following procedure:

Group 1: 10 $\mu$g intraperitoneal of β-gal-coccidiosis in PBS

Group 2: 10 $\mu$g intraperitoneal of β-gal-coccidiosis+CFA

Group 3: 10 $\mu$g intraperitoneal of lpp-coccidiosis in PBS

Group 4: 10 $\mu$g intraperitoneal of lpp-coccidiosis+CFA

The results are as follows:

lozenges: preimmune serum squares: mean of the 4 sera of group 1
circles: mean of the 4 sera of group 2
crosses: mean of the 4 sera of group 3
triangles: mean of the 4 sera of group 4

EXAMPLE 1

Construction of recombinant vectors containing the *P. aeruginosa* lipoprotein

Materials and Methods a. Construction of the vectors containing the lipoprotein

A vector pLPI, obtained by inserting a 2.94 kb SalI nucleotide sequence of the OprI gene encoding the *P. aeruginosa* lipoprotein into the XhoI site of the vector pKT240, was used. pLPI1 (Cornelis P. et al. Molecular Microbiology (1989) 3(3) 421–428) therefore contains the open reading frame of the sequence encoding the *Pseudomonas aeruginosa* lipoprotein.

In a first instance, the unwanted restriction sites present on the plasmid comprising the open reading frame of the lipoprotein were removed by digestion with the enzyme Bal31. As regards the plasmid pLPI1, a cut with the restriction enzyme Sst1 was made prior to the controlled digestion with Bal31. The digestion leads to the production of pLPI34 which differs from pLPI1 in the suppression of a number of chosen restriction sites. In particular, the unique EcoRI and HpaI sites were removed, as well as the two SphI sites of the vector.

Oligonucleotides were then defined which contain restriction sites which were not present in the initial plasmid or in the open reading frame of the lipoprotein. These polylinker oligonucleotides were synthesized on a solid phase using the phosphoramidite technique, in the form of two complementary oligonucleotides, in an Applied Biochemicals synthesizer.

The hybridization of the two oligonucleotides and the ligation with the vector cut with the enzyme SphI were then carried out. Two vectors pLPI35 and pLPI36 were thus obtained depending on the orientation of the polylinker inserted.

The cloning of the polylinker was then checked by restriction analysis of the lipoprotein fragment previously amplified by PCR.

The checking of the production of a complete lipoprotein in the external membrane, after transforming given cells with the vector, was carried out by Western blotting.

Another vector, constructed from the plasmid pKK233-2 (Aman E. et al., 1985, Gene 40:183–190) was used.

In a first instance, the EcoRI site of the expression vector pKK233-2 (Pharmacia) was removed by digesting the vector with the enzyme EcoRI and then filling with a Klenow fragment and religating.

The vector pKK233* was thus obtained into which lipoprotein-encoding fragments, modified by the polylinkers as obtained from pLPI35 and pLPI36, were cloned, these fragments having been previously amplified by PCR. The primers used for the PCR reaction corresponded to the beginning and the end of the ORF sequence as described by De VosD et al., J. Gen. Microbiol. 139 (1993) 2215–2223. The second primer used did not contain the two STOP codons of the oprI gene. The cloning was carried out by ligating the blunt ends into the NcoI site previously filled with a Klenow fragment, downstream of the ribosome-binding site and of the tac promoter.

The cloning of the fragment was checked by restriction analysis of the plasmids obtained, pVUB-1 and pVUB-2.

The possibility of inducing the expression of the lipoprotein was checked after induction with IPTG.

b. Growth of ASFV, purification of the virus and extraction of the DNA

The ASFV/L60 virus was cultured on pig macrophages and then recovered and concentrated by centrifugation. The virus was then purified by centrifugation in discontinuous sucrose gradients. Extraction of the virus DNA was carried out with the aid of proteinase K and phenol treatments.

Restriction of the purified DNA by the enzyme EcoRI confirmed the origin of the DNA.

c. Cloning of the ASFV DNA into the vectors containing the lipoprotein

The ASFV virus DNA was restricted with Sau3A (|GATC) or HaeIII (GG|CC). The plasmids pLPI35 and pLPI36 were also restricted with the enzyme BglII (compatible with the Sau3A fragments) or with HpaI (blunt ends, for ligation with the HaeIII fragments).

The ligation and the transformation of the host cells were then carried out.

The 2000 clones obtained were distributed into microtiter plates and subcultured.

The clones were subjected to colony hybridization with ASFV Sau3A fragments labeled with digoxigenin (Boehringer Mannheim) and the labeled clones were detected under light using the phosphatase AMPPD substrate.

The positive clones were then tested with two monoclonal antibodies against the lipoprotein, one reacting with the clones containing an insert in lpp and the other not reacting with the fusion protein (lpp modified by the insert).

The proteins of the external membrane of the most promising clones were prepared and analyzed by SDS-PAGE and Western blotting with a monoclonal antibody which recognizes the fusion protein.

To test the immunoproliferative response, external membranes of *E. coli* not expressing lpp (lpp−) and of *E. coli* modified with the plasmids pLPI35 and pLPI36 as well as clones producing the lpp-ASFV fusion were prepared.

d. Development and characterization of monoconal antibodies against the lipoprotein FI mice were immunized by injecting preparations of external membranes of *Pseudomonas aeruginosa* in complete Freund's adjuvant. These injections were carried out into mouse foot pads. 9 days later, a fusion of the lymphocytes collected from mice immunized with myeloma cells NSO was performed. 10 to 14 days following this fusion, the hybridomas were tested by ELISA on microtiter plates on which *P. aeruginosa* external membranes had been spread out.

The positive clones were detected by an ELISA test with external membranes of *E. coli* (pKT240 lpp−) and of *E. coli* (pLPI1 lpp+).

The cloning of the hybridomas having an anti-lpp activity was carried out by limiting dilution and expansion. The clones were then grown in mice. The determination of the nature of the epitope recognized was carried out by generating deletions in the lipoprotein gene, by digestion with Bal 31.

A test for detecting the reaction of various monoclonal antibodies produced by these hybridomas, with the various derivatives of the lipoprotein, including the fusion proteins, was carried out. The most promising monoclonal antibodies were then purified.

Results a. Development of the recombinant vectors containing the *P. aeruginosa* lipoprotein A first set of cloning vectors was developed with the *P. aeruginosa* lipoprotein (lpp) gene, cloned into a low-copy number vector, the plasmid pKT240. After removing certain restriction sites from the vector by digestion with Bal 31, polylinkers were defined, in the form of oligonucleotides containing unique restriction sites for the cloning in view of the insertion in the same reading frame as that of the lipoprotein and under conditions which make it possible not to change significantly the structure of the protein.

The polylinkers containing SphI extensions were introduced into the unique SphI restriction site present near the end of the lpp open reading frame (ORF). This open reading frame contain 250 bp. The various vectors obtained, differentiated according to their restriction sites, were as follows:

pLPI35: HpaI, EcoRI, BglII.

pLPI36: BglII, EcoRI, HpaI.

pLPI37: XhoI, SacI, XbaI, ClaI, BglII, XmaI, SmaI.

pLPI38: SmaI, XmaI, BglII, claI, XbaI, SacI, XhoI.

In these vectors, a complete lipoprotein was able to be expressed constitutively under the control of its own promoter.

This lipoprotein was, like the native lipoprotein, present in the external membrane of *E. coli* cells used as hosts, as shown by SDS-PAGE electrophoresis and the Western blot tests with anti-Lpp monoclonal antibodies.

In order to make the controlled expression of the protein possible, a clone was prepared with the expression vector pKK233-2. Firstly, the EcoRI site was removed from this vector by digestion with EcoRI, filing with a Klenow fragment and religating. The fragment containing the open reading frame of the plasmids pLPI35 and pLPI36 was amplified by PCR and subcloned into the NcoI site previously filled with the Klenow fragment of the modified plasmid pKK233-2, downstream of the tac promoter. The following vectors were obtained:

pVUB-1: HpaI, EcoRI, BglII pVUB-2: BglII, EcoRI, HpaI.

The LB medium allows the induction of the expression of lpp because it contains yeast extract, the nature of whose composition allows the induction of the lactose operon (by becoming attached, like IPTG, to the repressor lacI). It is therefore preferable to work in a defined medium, regardless of its nature (CAA, M9, and the like). The addition of glucose makes it possible, in addition, to exert a catabolic repression. It is moreover impossible to obtain transformants of pVUB1 or pVUB2 in LB+Ampicillin (Ap) medium, these transformants being only obtained in LB+glucose+Ap medium or in M9+Ap or CAA+Ap medium. On the other hand, some clones containing an insert can be obtained by direct transformation in LB medium (lower toxicity).

In an LB culture medium, the expression was not repressed in the absence of IPTG and led to cell death.

b. Growth and purification of ASFV-L60 and extraction of the virus DNA

Cultures of macrophages infected with the virus were used to collect $10^{10}$ $CPE_{50}$ of ASFV-L60. Since the mean titer of infected macrophages in the culture was $10^6$ $CPE_{50}$/ml, it was necessary to collect the equivalent of 10 liters of supernatant in order to have enough virus. The supernatants were collected separately and centrifuged in order to obtain the virus in the form of pellets.

The virus was purified by centrifugation in the presence of discontinuous sucrose gradients and subjected to a DNAase treatment in order to remove the pig DNA. The band containing the virus was recovered, recentrifuged and washed.

The viral DNA was extracted by treating with proteinase K and phenol extractions. The ASFV DNA was visualized by agarose gel electrophoresis in the form of a single band of about 200 kb while a low-molecular weight DNA (resistant to RNase) was also observed in the form of a cloud at the bottom of the gel, probably corresponding to the pig DNA degraded with the DNAase.

The restriction profile with EcoRI made it possible to see discrete bands corresponding to the profile previously observed for the ASFV/L60 DNA. Similarities were also observed with the profiles published for the ASFV DNA although differences were observed.

c. Cloning of the ASFV fragments into pLPI35 and pLPI36

The ASFV DNA was restricted with Sau3A and ligated into the two lpp-containing vectors pLPI35 and pLPI36 previously cut with BglII. Another part of the ASFV DNA was restricted with HaeIII and ligated by its blunt ends with these same vectors previously cut with HpaI.

After ligation and transformation, about 2000 clones were distributed into the microtiter plates and replicated and then hybridized with ASFV Sau3A fragments labeled with digoxygenin in the presence of an excess of unlabeled cut pig DNA.

45 positive clones were detected and 12 of them were selected. The external membranes were prepared and the proteins were separated by SDS-PAGE. The gels were either stained with coomassie blue or deposited on nitrocellulose in order to carry out an immunodetection. Two clones produced large fusion proteins, one produced a 25 kDa protein and another a 70 kDa protein.

A PCR amplification of these two clones revealed the presence of an inserted fragment of 0.8 kb for the clone producing the 25 kDa protein and of 2.5 kb for the clone producing the large fusion protein.

d. Production and characterization of monoclonal antibodies against the *P. aeruginosa* lipoprotein More than 20 hybridomas obtained exhibited a specific reaction with the *P. aeruginosa* lipoprotein without cross-reacting with the lipoproteins of enterobacteria. Analysis of the epitopes was carried out on lipoproteins gradually truncated by their C-terminal end (after SphI digestion of the plasmid pLPI34, followed by digestion with Bal31, religation and transformation of host cells). This made it possible to reveal that certain antibodies detected an N-terminal epitope whereas others reacted with a C-terminal epitope.

One of the monoclonal antibodies, KF9, recognized only the pLPI36 lipoprotein modified by the insertion of 10 amino acids corresponding to the polylinker, but did not recognize derivatives of the plasmid containing longer inserts.

This monoclonal antibody was therefore of interest for application to the screening of clones to detect the presence of inserted sequences. Two other monoclonal antibodies, QB2 and FA2.5 could detect the fusion proteins.

Discussion

It has therefore been demonstrated that it is possible to use the *Pseudomonas aeruginosa* lipoprotein gene as antigen for the expression, at the surface of recombinant cells, of chosen amino acid sequences. The introduction of polylinkers containing various restriction sites can also be carried out at the level of the sequence encoding lpp, without altering the level of expression or the location of the protein in the external cell membrane.

Two types of vectors were developed, a first category allowing constitutive expression and a second category leading to the controlled expression of the fusion protein obtained from lpp, itself modified by the insertion of a determined sequence. Certain monoclonal antibodies facilitated the screening of the recombinants by not exhibiting any reaction with the clones having the insert of the chosen amino acid sequence in the lipoprotein gene or, on the contrary, other antibodies allowed the detection of fusion proteins.

EXAMPLE 2

Isolation and characterization of a recombinant clone encoding an *Eimeria stiedae* antigen (Coccidiosis)

Introduction

Coccidiosis is a disease caused in chickens and in rabbits by a protozoal parasite of the Eimeria gene which generally invades the cells of the digestive tube and of the associated glands.

This disease causes enormous economic consequences for the small animal breeding industry.

Medical prophylaxis presently consists of using systematically coccidiostatic products in the feed for young animals, but major secondary problems have appeared, due in particular to the development of Eimeria strains which are resistant to the drugs.

Consequently, particular attention was paid to the production of new methods of controlling coccidiosis. This attention has been increasingly orientated toward immunoprophylaxis which corresponds to the study of biological vaccines for controlling these parasites.

The following results relate to the species *Eimeria stiedae*, a species which is pathogenic in rabbits.

Of the 9 species which infect the intestinal tract, *Eimeria stiedae* is the only species which develops in the bile ducts.

In this hepatic disease, the liver is considerably hypertrophic and its surface is marked by whitish nodes of variable size.

Methodology and Results

1. Parasite

This study consists, firstly, infecting 5-week old rabbits with *E. stiedae* sporulated oocysts. Three weeks after the infection, the oocysts are isolated from the liver and the bile ducts.

2. Extraction of the *E. stiedae* DNA

The *E. stiedae* DNA was extracted from sporozoites.

In a first instance, oocysts were isolated from the liver and the bile ducts of the rabbits infected with *E. stiedae* ($2 \cdot 10^8$ oocysts/ml).

The oocysts were then washed and placed in 2% potassium dichromate at room temperature for a period of 48 h, in order to obtain sporulation.

The sporulated oocysts were then washed until the potassium dichromate disappeared and ground in PES:

Nacl: 8 g

KCl: 0.2 g $Na_2HPO_4H_2O$ 2.07 g $KH_2PO_4$: 0.24 g

This grinding is done mechanically with the aid of a "Potter" in order to allow the liberation of the sporocysts.

The sporocysts were incubated in 0.25% trypsin and 0.1% glycodeoxycholic acid, in order to allow the liberation of the sporozoites.

The incubation was carried out on a water bath at 41° C. for 1 h, with stirring. The mixture was then centrifuged for 10 minutes at 3000 rpm, and the pellet containing the sporozoites recovered.

The sporozoites isolated were lyzed with:

10 mM Tris pH8

25 mM EDTA 100 mM Nacl

1% SDS

Proteinase K was then added to a final concentration of 100 µg/ml.

Incubation on a water bath at 37° C. was then carried out for 3 h followed by successive addition of:

1 volume of phenol and then centrifugation at room temperature for 10 minutes (2×);

2 volumes of 100% ethanol

The precipitate was then placed at −70° C. for 30 minutes.

The mixture was centrifuged for 15 minutes at 4° C. and then the pellet was washed with 70% ethanol, dried and dissolved in TE, pH8:

10 mM Tris 1 mM EDTA

The concentration of DNA obtained was determined by the optical density at 600 nm.

3. Construction of a genomic library

A genomic DNA library was constructed in the insertion and expression vector lambda gt11 (EcoRI site). Rabbit anti-sporozoite serum was used to screen the library and to identify the recombinants expressing the *E. stiedae* antigens.

A positive clone was isolated. The extraction of the DNA contained in the recombinant phage made it possible to identify a 1.2 kb insert (E. stR1).

4. Preparation of the β-galactosidase fusion protein

The preparation of the recombinant antigen was carried out using lambda gt11 lysogens.

The fusion protein was able to be purified directly by electrophoresis on an SDS-PAGE gel.

The protein obtained (gel estimation) is 138 kd, of which 22 kd correspond to part of the protein of the parasite.

5. Antiserum

For the production of the antiserum specific for the E. stR1 recombinant antigen, SPF rabbits (specific pathogen free from INRA, France, were immunized at 3 week intervals with 3 doses of 100 µg of electroeluted fusion protein.

The first dose was emuslified with complete Freund's adjuvant and the following doses with incomplete Freund's adjuvant. The serum was obtained 10 days after the last immunization. This serum was tested by indirect immunofluorescence on sporozoites dried on slides and by Western blotting on a crude sporozoite lysate.

Immunofluorescence

The test reveals a positive reaction of the serum at the level of the surface of the *E. stiedae* parasite; but on live sporozoites, the reaction is negative. This demonstrates that the antigen is not exposed at the surface of the parasite.

Western blotting

The test carried out on a crude lysate of sporozoites of three different species:

*stiedae:* hepatic coccidiosis

*magna:* hepatic intestinal

*intestinalis:* hepatic intestinal demonstrates that the antiserum (SPF and E. stR1) recognizes a predominant protein of 40 kd.

A serum obtained before immunization was used as negative control.

On the extracts of nonsporulated oocysts of *E. stiedae,* the antiserum (SPF and E. stR1) also reacts with a band of 40 kd.

This explains that the antigen is not synthesized at the sporozoite stage of the parasite since it is already present in the nonsporulated oocysts.

6. Sequence of the E. stR₁ DNA fragment

The insertion of the E. stR1 DNA fragment was used to transform the plasmid pUC18 and the clone was sequenced, after having carried out a deletion cloning of the genomic fragment with the enzyme Exonuclease III.

The sequence was established according to the Sanger method.

The sequence of this 1.2 kb fragment revealed an open reading frame of 741 nucleotides which starts at the EcoRI site.

It is a sequence which does not exhibit repetitive nucleotides.

The deduced protein at a length of 247 amino acids with a molecular weight of 27.5 kd.

The size of the fusion protein produced by this clone indicates that 62% of the total 1.2 kb insert encodes the parasite protein.

7. Cloning into the vector pVUB-1

In order to amplify the promising protein, the EstR1 genomic DNA fragment was cloned into the new expression vector pVUB-1.

This vector has the property of expressing the antigen as fusion protein with the *Pseudomonas aeruginosa* lipoprotein.

The reading frame of the pVUB-1 vector is compatible with the EcoRI site of the lambda gt11 phage, the cloning was therefore carried out inside the unique EcoRI site.

After transformation of the bacterium *E. coli* strain JM109, the recombinant clones were selected by hybridization and a positive clone was isolated (FIG. 4).

Analysis of this clone was carried out by plasmid DNA extraction and by Western blotting using immunodetection.

Extraction of plasmid DNA

The DNA, extracted from the positive recombinant clone, was digested with the restriction enzyme EcoRI in order to visualize the 1.2 kb insert (FIG. 5)

Western blotting

Induction of the expression of the fusion protein in the plasmid pVUB-1 was carried out by addition in the culture medium in the presence of IPTG.

The Western blot analysis made it possible to check the reaction of the fusion protein with the FA2.5 monoclonal antibody directed against the lipoprotein. The fusion protein detected has a molecular weight of 30–35 kd (FIG. 6).

Conclusion

The results of the immunodetection tests with the SPF and E. stR1 antisera on the crude extracts of sporozoites of the various species tested (*stiedae, magna, intestinalis* and *tenella:* the most pathogenic species in chickens) showed the existence of cross-reactions between these species of the genus Eimeria.

One advantage resulting from the use of the vector pVUB-1 would be the possibility of purifying the protein in sufficient quantity to allow the immunological and protective activity of the antigen to be tested.

To carry out this test, the recombinant protein, which encodes an antigen of the studied species *Emeria stiedae,* is amplified and used for vaccination tests.

These tests make it possible to know if such a "vaccine" could contain antigens common to the various species and thereby have a protective effect in rabbits.

The test relates to 3 different species:

*Eimeria stiedae*

*Eimeria magna*

*Eimeria intestinalis*

The parameters evaluated are:

the weight gain in the animal the feed conversion the percentage rejection of oocysts by the excrements.

EXAMPLE 3

A 48 bp insert, encoding the hepatitis B S2b T epitope and a B epitope, was cloned into the EcoRI site of the *Pseudomonas aeruginosa* lipoprotein. The insert was formed by hybridization of 2 complementary oligonucleotides, generating single-stranded extensions at each end, compatible with the cohesive ends generated after restriction with the enzyme EcoRI. The insert was defined such that it made it possible to maintain the open reading frame (ORF) of the lipoprotein as well as the insert itself (FIG. 8).

The vectors used were: pVUB1 (about 5 kb, large copy number containing a tac type promoter (for example the trc promoter) inducible by IPTG or lactose and its derivatives, resistant to ampicillin, and pLPI35 (13.5 kb, low copy number, constitutive expression of the lipoprotein, resistance to ampicillin).

The transformation of *E. coli* JM109 cells led to the production of more than 250 transformants selected on the basis of their ampicillin resistance properties. These transformants were screened in order to detect the presence of the epitope by colony blotting using a polyclonal antiserum directed against the S2b epitope in rabbits. All the antibodies which exhibited a cross-reaction were removed by adsorption against a cell lysate of *E. coli* JM109 transformed with pVUB1.

The secondary reaction was carried out with protein A coupled to horseradish peroxidase, using a 4-chloronaphthol medium (freshly prepared) and the BIORAD hydrogen peroxidase as colored substrate.

Among the 277 colonies tested, 6 reacted clearly positively.

The detection was also carried out by immunofluorescence.

EXAMPLE 4

Construction of a vector containing the *Pseudomonas aeruginosa* lipoprotein under conditions such that its expression can be controlled in *E. coli.*

1. Construction of the *P. aeruginosa* lipoprotein in the controlled expression vector pkk233-2, in *E. coli*

A gene encoding the *P. aeruginosa* lipoprotein was cloned into pKT240 and sequenced (Cornelis P. et al, 1989). Consequently, derivatives of this clone were constructed and inserted into a polylinker near the C-terminal end of the lpp structural gene (that is to say into pLPI35 and pLPI36). pLPI35 and pLPI36 contain an oligonucleotide of 30 mer with a unique restriction site for HpaI, EcoRI and BglII in opposite orientation, these sites having being inserted into the SphI site. This gene contains its own promoter, which leads to an overproduction of lpp in *E. coli* which causes a significant reduction in the growth rate of the bacterium.

In order to overcome this problem, the expression was considered under the control of the strong trc promoter of pKK233-2. Since the plasmid contains the trc promoter, the ribosome-binding site of lac-Z, and an ATG initiation codon, therefore the expression of the inserted lpp gene under the control of this promoter could be controlled by induction using IPTG.

Since a unique EcoRI site had been introduced into the polylinker of the lpp gene, the EcoRI site of the pkk233-2 vector had to be removed. The removal of this site was followed by ligation of the blunt ends such that the new derived plasmid pKKD no longer contained the EcoRI site. Using the plasmid pKKD, the construction of the lpp structural gene containing the polylinker was ligated into the NcoI site whose ends had been made blunt with the Klenow fragment. The recombinant clones PVUB1 and pVUB2 were obtained as derivatives of pLPI35 and pLPI36.

Figure 9:
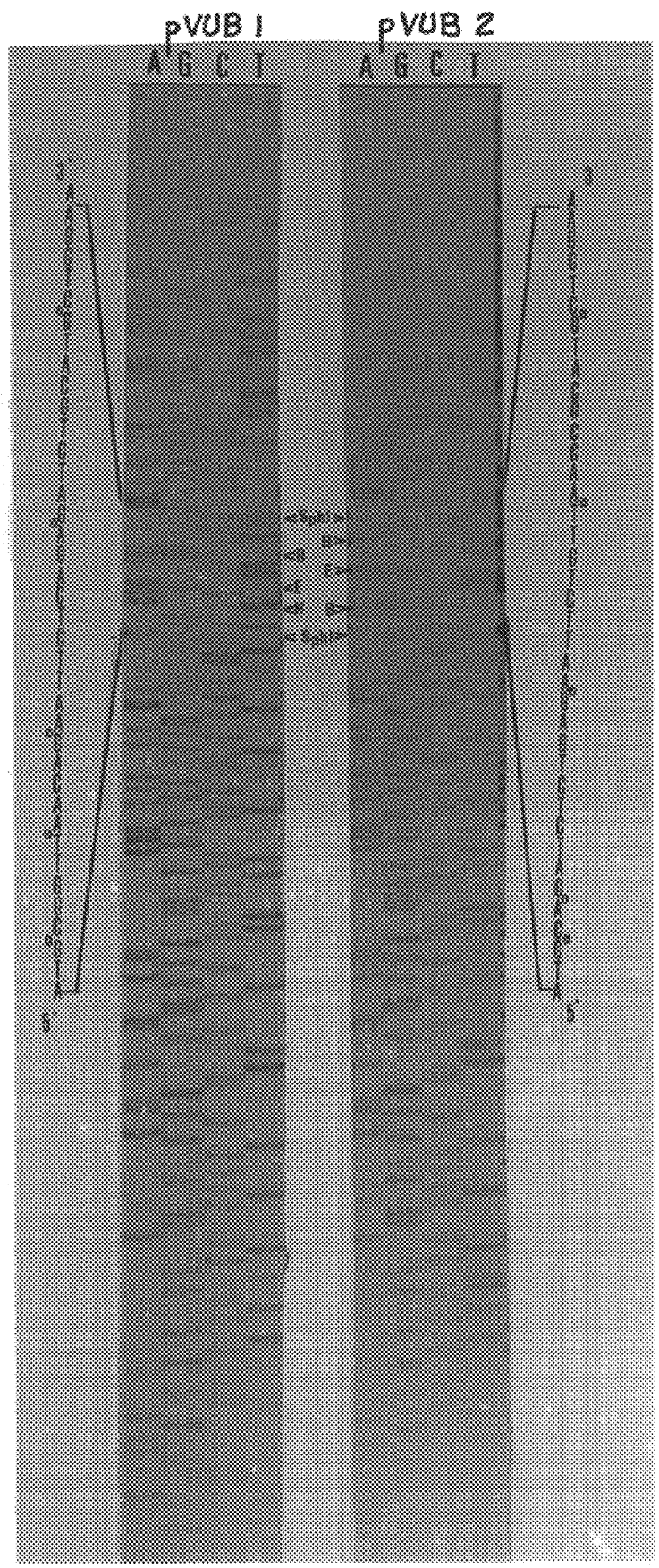

The cloning strategy is shown in FIG. 8 and the sequencing of pVUB1 and pVUB2, including the polylinker, is in FIG. 9.

EXAMPLE 5
Expression of lpp in *E. coli*

Figure 10:
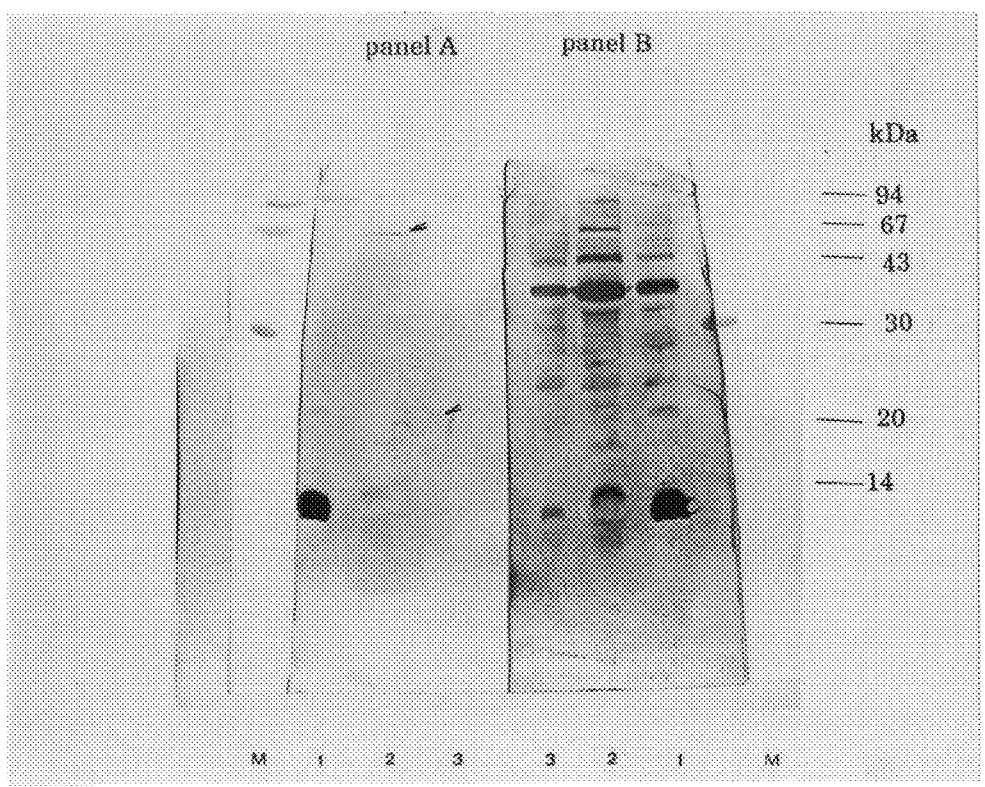

Monoclonal antibodies against the *P. aeruginosa* lpp were produced. Their characterization showed that some of them recognize epitopes of the N-terminal part (antibodies FA2.5, pE4.1) and others recognize an epitope close to the pVUB2 polylinker (antibody KF9). The KF9 antibody recognizes the Lpp of pLPI34 and nonspecifically that of pLPI36 or pVU2. Recombinant clones containing the lpp gene were screened by immunodetection of colonies. The controlled expression of the vectors pVUB1 and pVUB2 was carried out in either an M9 medium plus casamino acid or in an LB medium plus 1% glucose containing 100 μg/ml of ampicillin. The induction was performed with 1 mM IPTG (final concentration) or in the M9 medium containing the casamino acid or in the LB medium containing 100 μg/ml of ampicillin. Incubation was carried out at 37° C. for 3 to 6 hours. In order to determine the protein profile and to locate the lpp product, an external membrane preparation was made and analyzed either by Western blotting or by staining with comassie blue. FIG. 10 shows the protein profile and the production of lpp by detection with the FA2.5 antibody. The result shows a high production of lpp both in a free form and in a bound form.

In order to increase the production of lpp, iron(III) was added to the culture medium. The overproduction of lpp increased significantly in 50 and 100 μm of additional iron(III) (FIG. 10).

Figure 11:
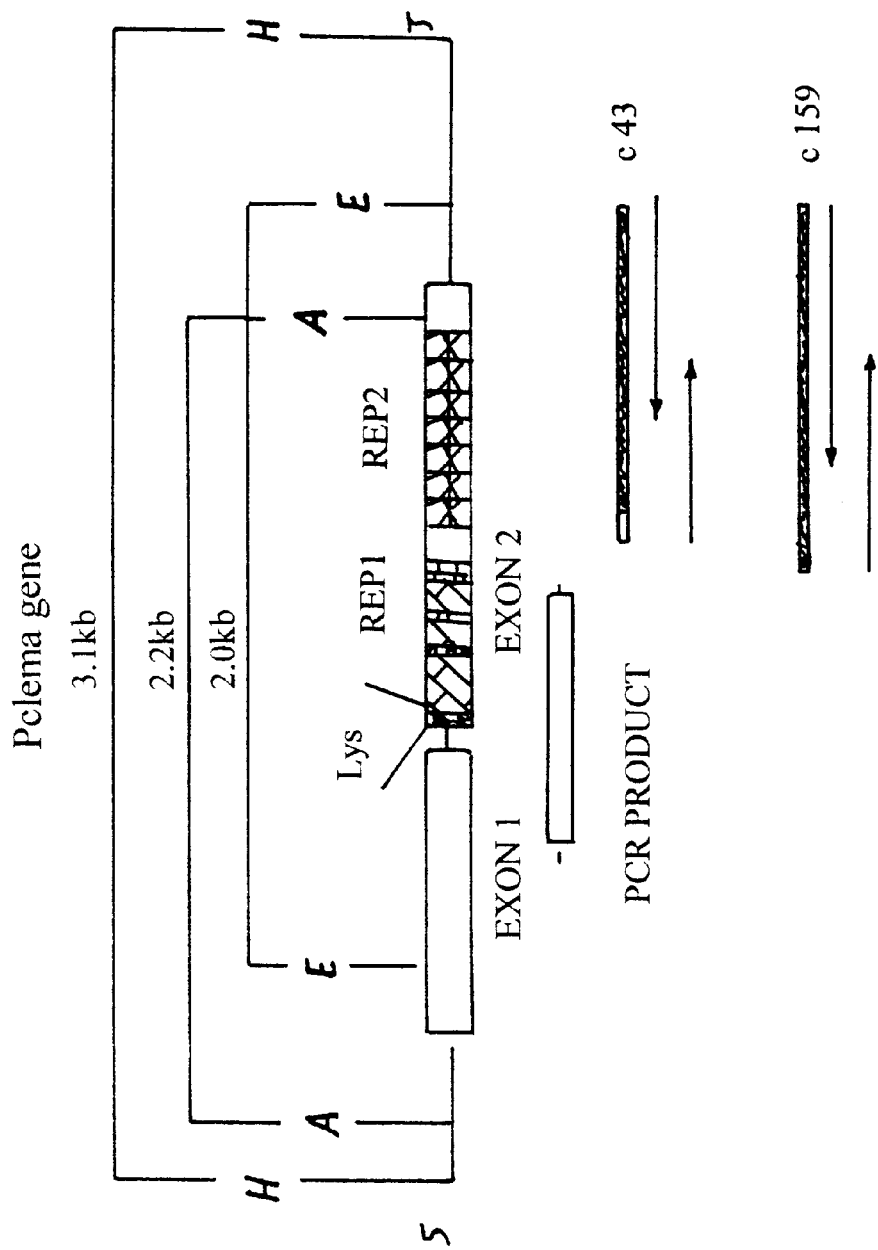

EXAMPLE 6
Expression of a fusion protein containing lpp and a malaria antigen A maleria antigen specific for the late stage was used. It is obtained from *Plasmodium chabaudi* which is responsible for malaria in rodents, making it possible to define a model for malaria in mice (Deleersnijder W. et al., Mol. Biochem. Parasitol. 43 (1990) 231–244). This antigen is associated with the membrane of infected erythrocytes and is called PcLEMA. The primary structure of the gene is given in FIG. 11. cDNA clones containing the C-terminal part were screened in a cDNA expression library constructed in lambda gt11 using a monoclonal antibody against this antigen. The inserts contain 650 and 600 bp respectively, in phase with the β-galactosidase gene, at the EcoRI site.

Figures 12A, 12B:
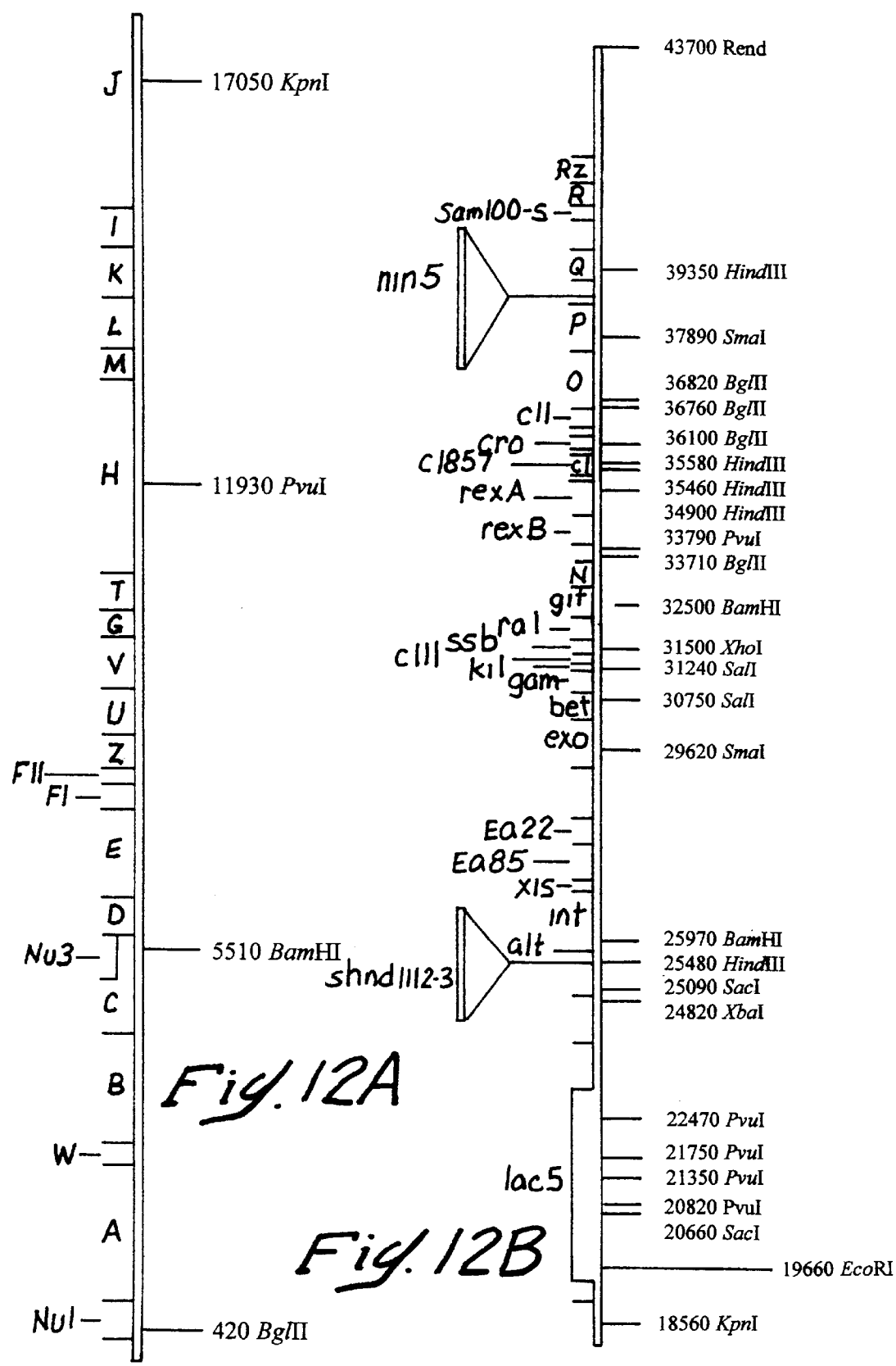
Figure 13:
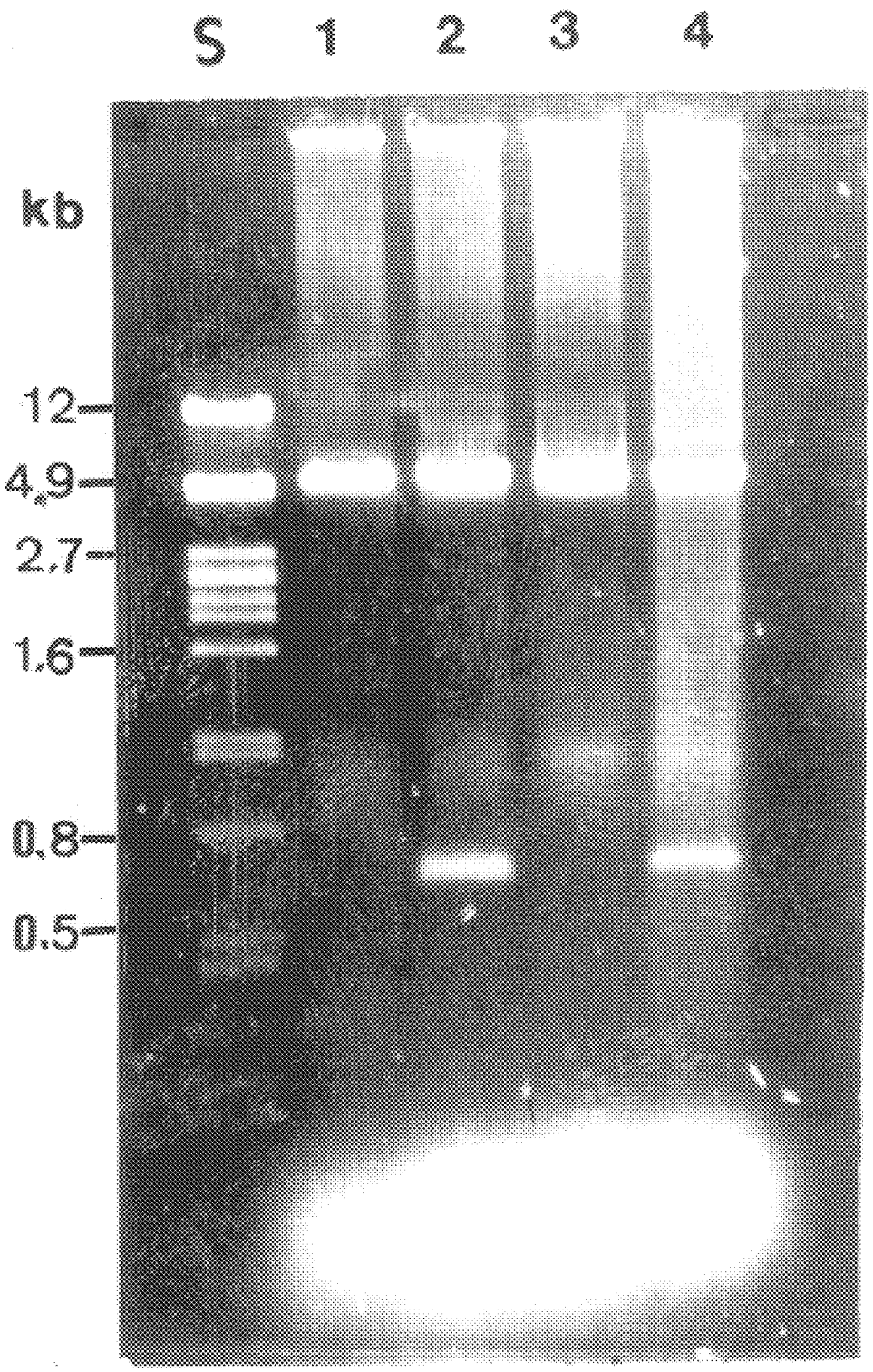
Figure 14A:
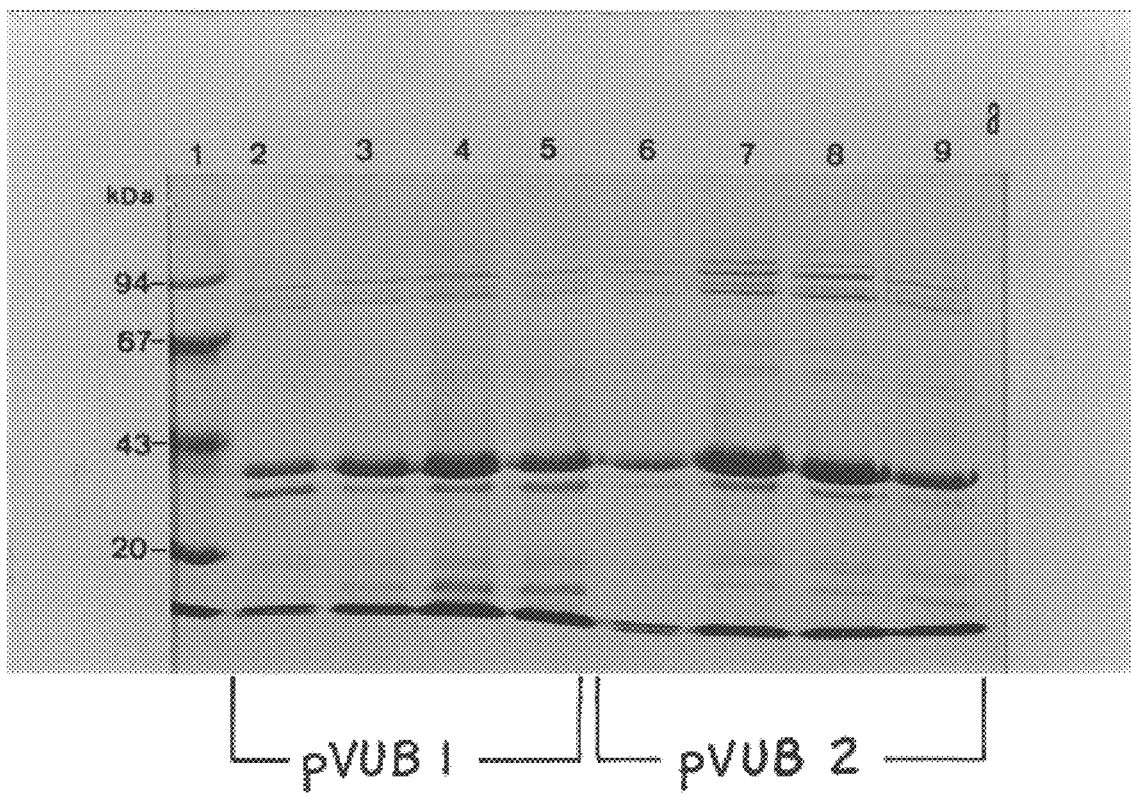
Figure 14B:
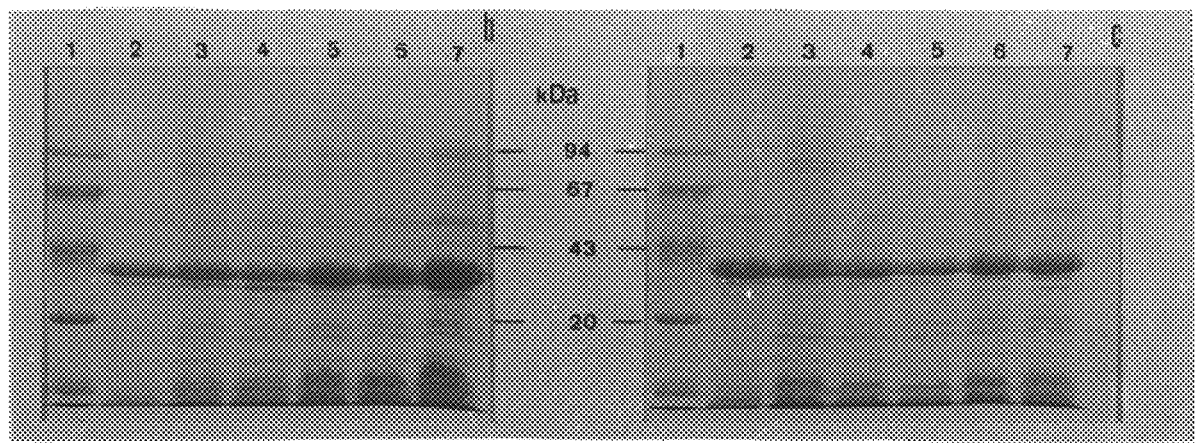
Figure 15:
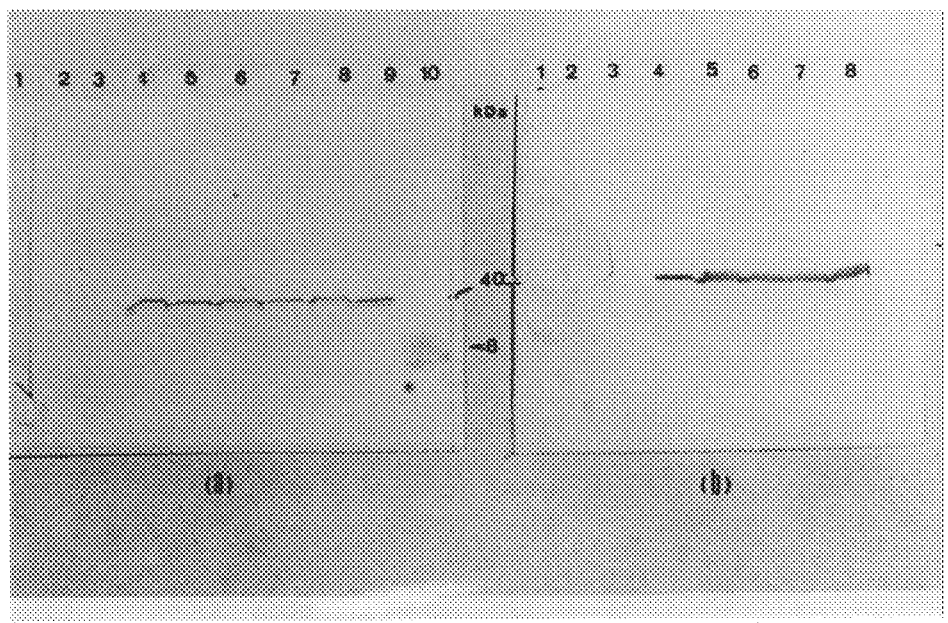
Figure 16:
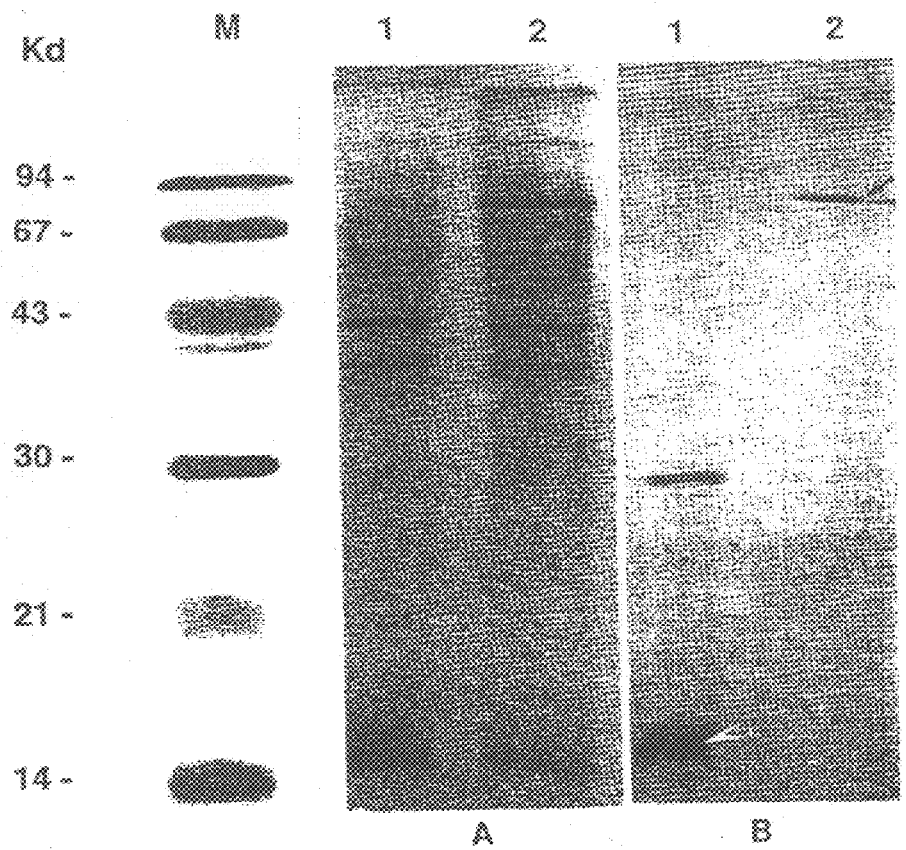

The vector pVUB1 contains an EcoRI site in the polylinker, which is compatible with an EcoRI site in the polylinker of the β-galactosidase gene of the vector lambda gt11 (FIG. 12). Accordingly, the 650 bp insert was excised with the enzyme EcoRI and directly subcloned either into pLPI35, or into pVUB1 at the EcoRI site. After immunological screening of the colonies, the recombinant clones were analyzed by extraction of the plasmid (FIG. 13) and Western blotting (FIG. 14).

The result shows that the product of the fusion of lpp with the malaria antigen in the controlled expression vector PVUB1 has a production yield greater than that obtained by expressing this same fusion protein with the aid of the vector pLPI35. The molecular weight of the fusion product is about 30 kDa (calculated $M_w$) (8 kDa for lpp at 22 kDa for the 650 bp insert), but the migration during SDS-PAGE electrophoresis is detected at about 40 kDa. This would correspond to an extensive region of tandem repeats having the pronounced hydrophilic character of the malaria antigen.

EXAMPLE 7
Cloning and expression of the surface glycoprotein gp63 of Leishmania in the vector PVUB2 containing the lipoprotein 1) Cloning of the gp63 gene The entire Leishmania major gp63 gene present on a 2.2 kb EcoRI fragment in the Blue Script PBS vector (stratagene) has been described by Button and MacMaster (1988), J. Exp. Med., 176, 724–729.

The PBS vector was digested with EcoRI and the 2.2 kb fragment was purified on a 1% agarose gel using the Geneclean kit (BIO 101 Inc., La Jolla, Calif.). The fragment was then ligated into the EcoRI site of pVUB2, which was in phase with the gp63 sequence. The vector pVUB2 had already been prepared by digestion with EcoRI, followed by treatment with Calf Intestinal Phosphatase (CIP), so as to avoid self ligation of the plasmid. pVUB2 was finally purified using a 1% agarose gel with the aid of the Geneclean kit. After transformation of *E. coli* JM109, the transformants were analyzed by restriction analysis and the clones containing the 2.2 kb fragment were selected as recombinants. The orientation of the fragment was also analyzed by restriction analysis.

2) Expression of the gp63 recombinant

The expression of the fusion protein by the recombinant clones was analyzed by SDS-PAGE electrophoresis. A gp63-expresing pVUB2 vector colony was cultured overnight in M9-CAA medium at 37° C. The culture was diluted and cultured at 37° C. with constant shaking until an optical density of 0.3 is obtained before adding IPTG (isopropyl B-D-thiogalactopyranoside) at 1 mM. After 5 to 6 additional hours at 37° C., the bacteria were recovered by centrifugation and the recombinant fusion protein was analyzed by SDS-PAGE electrophoresis.

3) Purification of the fusion protein containing gp63

The recombinant gp63 protein was expressed in one liter of culture, according to the technique described above. The proteins contained in the external membrane were prepared using a lysozyme and then an ultrasound treatment and were dissolved in 25 mM Tris-HCl at pH 8. The proteins were then solubilized in a sample of SDS buffer and separated by SDS-page electrophoresis on 6% gels. The gels were stained with coomassie blue at 0.06% in water and destained with water. The band corresponding to the fusion protein was cut out from the gel and purified by electroelution.

4) Production of antibodies against the recombinant gp63

70 μg of gp63 fusion proteins purified by electroelution were injected subcutaneously into two rabbits in the absence of complete Freund's adjuvant. The rabbits were subjected to a booster, twice with 60 μg of purified recombinant gp63 at 4 week intervals. Normal and immune sera were obtained from the immunized rabbits before and one week after the first and third immunization respectively.

EXAMPLE 8
Production of antibodies

1) With the coccidiosis protein (*Emeria stiedae*)

The fusion protein described in Example 2 was cut out of a 17.5% SDS-PAGE gel after migration of the proteins of the external membrane of an *E. coli* clone containing the recombinant plasmid described in the text and after induction of the culture with IPTG. The gel was stained with coomassie blue (0.06%) diluted in water. The fusion protein was then electroeluted according to the manufacturer's recommendations (Bio-Rad). At the same time, the same antigen, but fused with β-galactosidase (lambda GT11 clone) was prepared and electroeluted (using a crude extract of the E. coli clone).

Four groups of 4 Balb/C mice were prepared for the immunization experiments:

Group 1: 10 μg intraperitoneal of β-gal-coccidiosis in PBS

Group 2: 10 μg intraperitoneal of β-gal-coccidiosis+CFA

Group 3: 10 μg intraperitoneal of lpp-coccidiosis in PBS

Group 4: 10 μg intraperitoneal of lpp-coccidiosis+CFA

The injected volume was 150 μl each time.

Four weeks after the first immunization, a second immunization was carried out, this time without CFA, with the same quantity of protein; a third immunization was carried out 4 weeks after the second, still without CFA. Ten days after this last immunization, the mouse serum was collected and the presence of antibodies tested by ELISA on microtiter plates (NUNC) containing crude *Emeiria stiedae* extract obtained from sporulated oocytes (10 μg/well).

Figure 17:
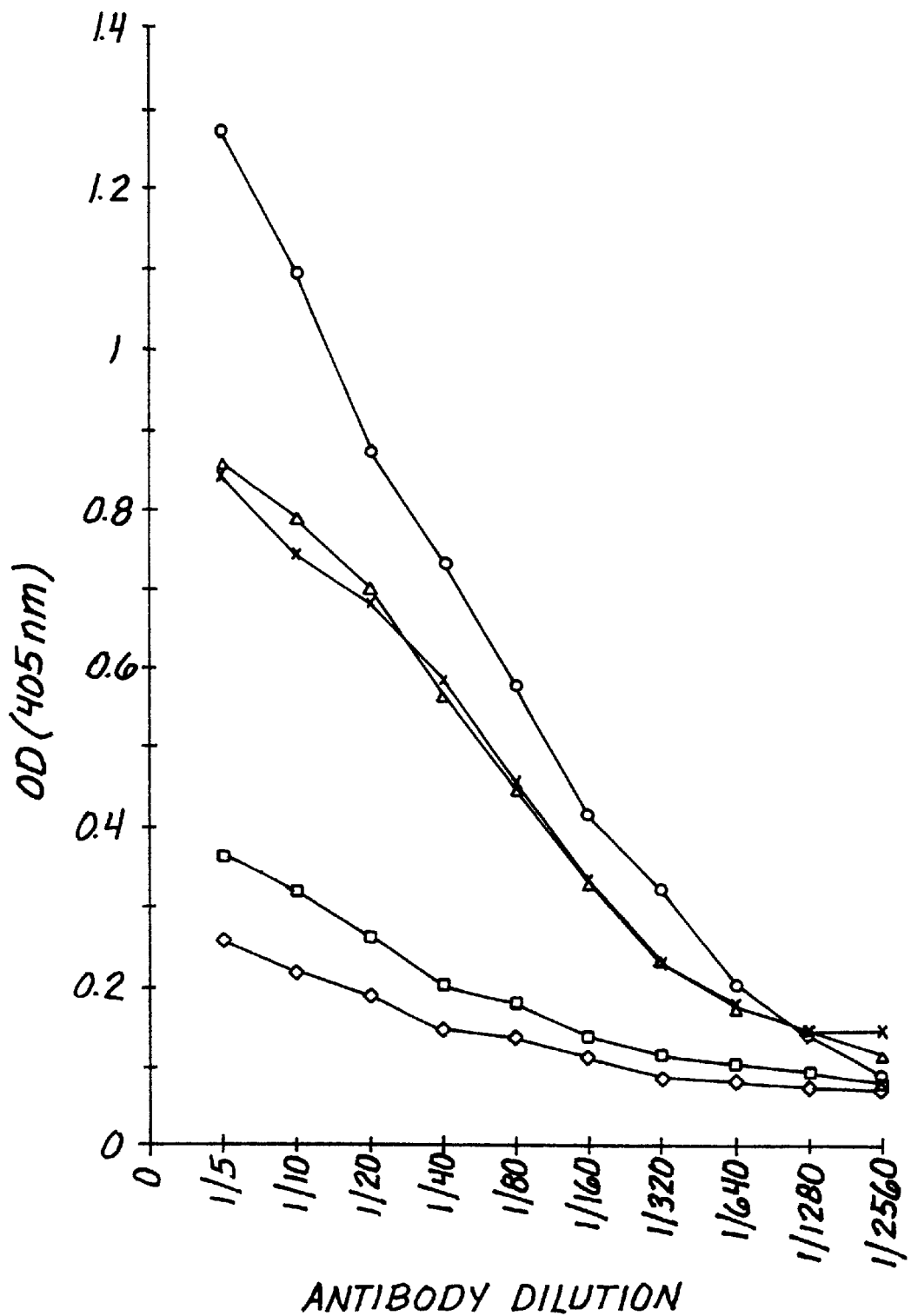

After saturating the plates with BSA, the sera are added at various dilutions, incubated for two hours and, after two washes with PBS-Tween, the secondary antibody (goat anti-mouse phosphatase) is added and the incubation is continued for 1 hour. After 5 washes, the phosphatase substrate is added (p-nitrophenyl phosphate) and the plate is read after incubating for half an hour at room temperature. The results are given in FIG. 17:

lozenges: preimmune serum squares: mean of the 4 sera of group 1 circles: mean of the 4 sera of group 2 crosses: mean of the 4 sera of group 3 triangles: mean of the 4 sera of group 4

2) With a *Plasmodium chabaudi* malaria antigen

The fusion protein produced from the clone pVUB and described in Example b was similarly eluted (see 1) and injected with or without CFA (20 μg of protein) into two rabbits. After the third injection according to a procedure identical to the preceding one, the sera were collected and absorbed against the lipoprotein itself. An ELISA was carried out with, as antigen, the lpp-malaria fusion protein (5 μg/well), as control, the lpp protein itself was used.

The results are as follows:

no reaction with lpp serum of rabbit immunized without adjuvant: 50% binding for the 1/1200 dilution serum of the rabbit immunized with adjuvant: 50% binding for the 1/1000 dilution.

EXAMPLE 9

Presentation of a hepatitis B S2B T epitope

The principle is to present either the fusion protein with the lipoprotein to antigen-presenting cells (in this case the TA3 strain which is a continuous B line) for half an hour and then to wash the cells and to incubate them with a T hybridoma recognizing the S2B T epitope overnight. If the B cell correctly presented the epitope to the hybridoma, the latter in turn secretes IL2. After incubation of the activated B cells and of the hybridoma, the supernatant was collected and added to CTL-L cells in order to measure the profileration induced by IL2 by incorporation of titrated thymidine. As control, the B line nonpreincubated or incubated with various quantities of the S2B peptide alone (not fused) was used. A typical experiment has been described below:

The TA3 cells were preincubated for 1½ hours ($10^6$ cells/tube) on ice.

They were then washed 4 times in RPMI+penicillin and streptomycin medium.

They were then preincubated with various concentrations of antigen:

(0, 20, 10, 2 μg of the fusion protein purified by electroelution)

(0, 30, 6, 3 μg of the pure peptide).

They were transferred into wells of microtiter plates in an amount of $5 \times 10^4$ cells per well in 200 μl.

After incubating for one and a half hours, the cells were again washed, transferred into wells of microtiter plates at $5 \times 10^4$ cells per well (in triplicate).

The hybridoma T cells (strain HB68) were then added at $2 \times 10^4$ cells to the wells already containing the preincubated cells.

The two types of cells were incubated overnight at 37° C.

The supernatants were collected for a conventional test of lymphoproliferation of mouse CTL-L cells (the other cells are also from mice) in the presence of $^3$H-thymidine.

The following results were obtained:

Antigen O: 2,354 cpm

Antigen S2B-lpp 2 μg: 10,393 cpm

Antigen S2B-lpp 10 μg: 26,832 cpm

Antigen S2B-lpp 20 μg: 44,130 cpm

Antigen S2B 3 μg: 1,438 cpm

Antigen S2B 6 μg: 760 cpm

Antigen S2B 30 μg: 5,035 cpm

Conclusion

Even for a high concentration of pure S2B peptide (it is necessary to take into account the fact that on a molar basis there is more S2B antigen presented than S2B-lpp), there is no good presentation to the T hybridoma, whereas the lpp fusion protein presents the epitope well.

We claim:

1. A recombinant vector for the cloning, expression, and exposure at the surface of the external membrane of Gram-negative bacteria of a heterologous polypeptide, said vector comprising a nucleotide sequence encoding a fusion protein consisting of the major lipoprotein of the external membrane of the *P. aeruginosa,* OprI, and the heterologous polypeptide.

2. The recombinant vector according to claim 1, wherein said vector is a plasmid.

3. The recombinant vector according to claim 1 or 2, wherein the lipoprotein OprI is heterologous in relation to the cell host containing the vector.

4. The recombinant vector according to claim 1 or 2, wherein the nucleotide sequence encoding said major lipoprotein is modified with one or more restriction sites.

5. The recombinant vector according to claim 1, wherein the expression of the nucleotide sequence encoding the heterologous polypeptide is constitutive.

6. The recombinant vector according to claim 1, which is plasmid pLPI34 deposited at BCCM (LMBP) under the No. LMBP2916.

7. The recombinant vector according to claim 1, which is plasmid pLPI35 or plasmid pLPI36.

8. The recombinant vector according to claim 1, which is vector pVUB1 or vector pVUB2.

9. The recombinant vector according to claim 1, wherein the nucleotide sequence encoding the heterologous polypeptide encodes an amino acid sequence containing one or more antigenic determinants or one or more haptens.

10. The recombinant vector according to claim 9, wherein the nucleotide sequence encoding the heterologous polypeptide encodes a type B epitope, a type T epitope or both, of determined antigens of pathogenic agents.

11. The recombinant vector according to claim 1, wherein the nucleotide sequence encoding the heterologous polypeptide encodes an amino acid sequence of a heavy chain of an antibody or of a light chain of an antibody.

12. The recombinant vector according to claim 1, wherein the nucleotide sequence encoding the heterologous polypeptide encodes an antibody consisting exclusively of heavy chains.

13. The recombinant vector according to claim 1, wherein the expression of the nucleotide sequence encoding the heterologous polypeptide is a controlled expression.

14. A recombinant Gram-negative bacterium host cell which is transformed by a recombinant vector according to claim 1.

15. The host cell according to claim 14, which is a strain of *E. coli*.

16. The host cell according to claim 14, which is a strain of *Alcaligenes eutrophus*.

17. The host cell according to claim 14, wherein the nucleotide sequence encoding the heterologous polypeptide encodes an antibody or an antibody fragment.

18. The recombinant Gram-negative bacterium host cell according to claim 14, which does not naturally express the *P. aeruginosa* OprI lipoprotein.

19. A recombinant protein which is the product of expression of a vector according to claim 1.

20. An immunogenic composition which comprises, as an active ingredient, at least one protein according to claim 19, or a host cell according to any one of claims 15 to 17.

21. A recombinant Gram-negative bacterium host cell which is transformed with a vector selected from the group consisting of pLPI34 (LMBP2916), pLPI35, pLPI36, pVUB1 and pVUB2.

22. A recombinant vector for the expression into a host cell and exposure at the surface of the host cell, of a heterologous nucleotide sequence, containing, at a site not essential for its replication, a first gene encoding the major lipoprotein of the external membrane of *P. aeruginosa*, OprI, and a heterologous nucleotide sequence which is introduced into said first gene at the level of the N-terminal part of the mature OprI lipoprotein, under conditions allowing the expression of this heterologous sequence and its exposure at the surface of the cell host.

23. A recombinant vector for the expression, into a host cell and exposure at the surface of the cell host, of a heterologous nucleotide sequence, containing, at a site not essential for its replication, a first gene encoding the major lipoprotein of the external membrane of *P. aeruginosa*, OprI, and a heterologous nucleotide sequence which is introduced into said first gene at the level of the N-terminal part of the mature OprI lipoprotein, 3 or 4 amino acids following the N-terminal end, under conditions allowing the expression of this heterologous sequence and its exposure at the surface of the external membrane of the cell host.

* * * * *